United States Patent
Takahata et al.

(10) Patent No.: US 9,370,628 B2
(45) Date of Patent: Jun. 21, 2016

(54) WIRELESS MICROACTUATORS AND CONTROL METHODS

(75) Inventors: Kenichi Takahata, Richmond (CA); Mohamed Sultan Mohamed Ali, Vancouver (CA); Somayyeh Rahimi, Austin, TX (US)

(73) Assignee: UNIVERSITY OF BRITISH COLUMBIA, Vancouver (CA)

( * ) Notice: Subject to any disclaimer, the term of this patent is extended or adjusted under 35 U.S.C. 154(b) by 1122 days.

(21) Appl. No.: 13/324,587

(22) Filed: Dec. 13, 2011

(65) Prior Publication Data

US 2012/0310151 A1    Dec. 6, 2012

Related U.S. Application Data

(60) Provisional application No. 61/493,488, filed on Jun. 5, 2011.

(51) Int. Cl.
*F16K 17/38* (2006.01)
*A61M 5/44* (2006.01)
*B29C 35/08* (2006.01)

(52) U.S. Cl.
CPC .......... *A61M 5/44* (2013.01); *B29C 2035/0811* (2013.01); *B29C 2035/0827* (2013.01); *Y10T 156/10* (2015.01)

(58) Field of Classification Search
CPC . A61M 5/44; Y10T 156/10; Y10T 29/49412; Y10T 29/49002; Y10T 29/49758; Y10T 29/4976; Y10T 74/11; Y10T 74/18704; B29C 2035/0811; B29C 2035/0827; F16K 5/025; F16K 5/045; F16K 49/002; F16K 99/004; F16K 99/0044; F16K 2099/0086; B01L 2400/0067; B01L 2400/0677

USPC ............ 137/72, 74, 76, 487.5, 833, 827, 828; 604/48; 251/11
See application file for complete search history.

(56) References Cited

U.S. PATENT DOCUMENTS

| | | | |
|---|---|---|---|
| 4,425,117 A | 1/1984 | Hugemann et al. | |
| 5,346,372 A * | 9/1994 | Naruse et al. | 417/379 |
| 6,382,254 B1 * | 5/2002 | Yang et al. | 137/807 |
| 6,491,061 B1 * | 12/2002 | Lopez et al. | 137/599.01 |
| 6,527,003 B1 * | 3/2003 | Webster | 137/15.18 |
| 6,626,417 B2 * | 9/2003 | Winger | F15C 5/00 251/129.01 |

(Continued)

OTHER PUBLICATIONS

Davis, B.A., "Investigation of the Thermomechanical Response of Shape Memory Alloy Hybrid Composite Beams," NASA/CR-2005-213929, pp. 1-135 (Oct. 1, 2005).

(Continued)

*Primary Examiner* — Craig Schneider
*Assistant Examiner* — Minh Le
(74) *Attorney, Agent, or Firm* — Foley & Lardner LLP

(57) ABSTRACT

Embodiments of the present technology include a micromachined implantable drug delivery devices, grippers, and syringes that are wirelessly powered and controlled by frequency tuning of external radiofrequency (RF) magnetic fields. An illustrative device can be designed and constructed with passive circuitry and microvalves that operate without batteries, e.g., through thermal actuation of hydrogel microvalves and/or shape-memory alloy members. The frequency selectivity in the device control provides not only a path to achieving reliable and safe operation of drug delivery but also potential applications for selective delivery of multiple drugs.

15 Claims, 38 Drawing Sheets

(56) References Cited

U.S. PATENT DOCUMENTS

| | | | |
|---|---|---|---|
| 6,935,165 B2* | 8/2005 | Bashir | C12Q 1/00 73/61.75 |
| 7,011,793 B2* | 3/2006 | Zhou et al. | 422/503 |
| 7,709,544 B2* | 5/2010 | Doyle et al. | 522/3 |
| 7,763,014 B2 | 7/2010 | Houzego et al. | |
| 7,783,144 B2* | 8/2010 | Chigrinov et al. | 385/30 |
| 7,817,030 B2* | 10/2010 | Hood et al. | 340/539.12 |
| 7,926,514 B2* | 4/2011 | Park et al. | 137/828 |
| 8,002,235 B2* | 8/2011 | Vyawahare et al. | 251/11 |
| 8,281,815 B2* | 10/2012 | Park et al. | 137/828 |
| 8,828,209 B2* | 9/2014 | Gorfinkel et al. | 204/453 |
| 9,193,816 B2* | 11/2015 | Jiang | C08L 51/10 |
| 2001/0048088 A1* | 12/2001 | Polla et al. | 251/129.06 |
| 2004/0007051 A1 | 1/2004 | Bashir et al. | |
| 2004/0094733 A1* | 5/2004 | Hower et al. | 251/11 |
| 2004/0188648 A1* | 9/2004 | Xie et al. | 251/11 |
| 2005/0116798 A1 | 6/2005 | Bintoro et al. | |
| 2005/0177223 A1 | 8/2005 | Palmaz | |
| 2007/0227592 A1* | 10/2007 | Allen et al. | 137/72 |
| 2008/0154179 A1 | 6/2008 | Cantor et al. | |
| 2010/0055394 A1* | 3/2010 | Hua et al. | 428/138 |
| 2010/0093559 A1* | 4/2010 | Fan et al. | 506/9 |
| 2011/0121196 A1* | 5/2011 | Yeo et al. | 250/428 |
| 2011/0124049 A1* | 5/2011 | Li et al. | 435/91.2 |
| 2011/0186165 A1* | 8/2011 | Borenstein et al. | 137/833 |
| 2012/0126154 A1* | 5/2012 | Den Dulk et al. | 251/11 |
| 2012/0135235 A1* | 5/2012 | Bong et al. | 428/402 |
| 2013/0133757 A1* | 5/2013 | Akinwande et al. | 137/74 |
| 2014/0287966 A1* | 9/2014 | Gray et al. | 506/39 |

OTHER PUBLICATIONS

International Preliminary Report on Patentability for PCT/US2011/064665 mailed on Mar. 6, 2014.

International Search Report and Written Opinion for PCT/US2011/064665 dated Jul. 13, 2012.

E.H. Sarraf, G.K. Wong, K. Takahata, "Frequency-Selectable Wireless Actuation of Hydrogel Using Micromachined Resonant Heaters toward Implantable Drug Delivery Applications," 15th IEEE Int'l Conf. Solid State Sensors, Actuators and Microsystems (Transducers 2009), Denver, CO, USA, Jun. 2009, pp. 1525-1528.

M.S. Mohamed Ali, K. Takahata, "A Wirelessly Controlled Shape-Memory-Alloy MEMS Gripper Microfabricated Using an Electroplating-Based Bonding Process," Solid-State Sensor, Actuator and Microsystems Workshop (Hilton Head 2010), Hilton Head Island, SC, USA, Jun. 2010, pp. 396-399.

M.S. Mohamed Ali, K. Takahata, "Frequency-Controlled Wireless Shape-Memory-Alloy Microactuators Integrated using an Electroplating Bonding Process," Sensors and Actuators A: Physical, 163(1), Aug. 2010, pp. 363-372.

M.S. Mohamed Ali, K. Takahata, "Selective RF Wireless Control of Integrated Bulk-Micromachined Shape-Memory-Alloy Actuators and its Microfluidic Application," 24th IEEE Int'l Conf. Micro Electro Mechanical Systems (MEMS 2011), Cancun, Mexico, Jan. 2011, pp. 1269-1272.

M.S. Mohamed Ali, K. Takahata, "Wireless microfluidic control with integrated shape-memory-alloy actuators operated by field frequency modulation," J. Micro Micromechanics and Microengineering, J. Micromechanics and Microengineering, 21, 2011, 075005 (10pp).

S. Rahimi, E.H. Sarraf, G.K. Wong, K. Takahata, "Implantable Drug Delivery Device Using Frequency-Controlled Wireless Hydrogel Microvalves," Biomedical Microdevices, 13(2), 2011, pp. 267-277.

S. Rahimi, K. Takahata, "A Wireless Implantable Drug Delivery Device with Hydrogel Microvalves Controlled by Field-Frequency Tuning," 24th IEEE Int'l Conf. Micro Electro Mechanical Systems (MEMS 2011), Cancun, Mexico, Jan. 2011, pp. 1019-1022.

* cited by examiner

WIRELESS MICROACTUATORS AND CONTROL METHODS

CROSS-REFERENCE TO RELATED PATENT APPLICATION

This application claims the benefit of U.S. Provisional Application No. 61/493,488, filed Jun. 5, 2011, the contents of which are incorporated herein by reference in their entirety.

BACKGROUND

Micro-Electro-Mechanical Systems (MEMS) for drug delivery applications have attracted significant interest leading to extensive investigation. Implantable MEMS devices for drug delivery are designed for controlled release of drugs locally at diseased sites through miniaturized devices. Site-specific drug delivery offers more effective therapies for non-systemic diseases or disorders as compared with conventional methods using systemic drug administration that can cause negative impacts on non-diseased areas of the body.

For implantable devices, the elimination of a wired interface is advantageous. Implantable devices with active circuitry require batteries or other power supplies that must be recharged or replaced for continued operation. Passive implantable devices do not require batteries, but suffer from implementation issues including small actuation force and stroke, use of high voltages, micromachining and integration of ferromagnetic materials, and actuator/system packaging. For example, one type of passive device uses electrostatic force to drive an actuator and usually requires high voltages which are generated wirelessly.

Some systems rely on thermal actuation induced by energy-beam-assisted heating. These systems tend to be complicated and large. In cases where the target actuator makes a movement, for example in micro-robotic applications, the beam control system needs to include an automated function that precisely directs the beam to the moving target to ensure continuous actuation. These difficulties increase further when multiple actuators are involved. Moreover, thermal actuation induced by energy-beam-assisted heating is ineffective when there is an object obstructing the beam path; thus, energy-beam-assisted heating cannot be used to actuate devices implanted inside the body.

SUMMARY

Embodiments of the present technology include a microfluidic device and methods of using a microfluidic device. The microfluidic device includes a reservoir to hold a substance, such as a powder, fluid, or drug, that may be released through a release hole in the reservoir. The device also includes a hydrogel microvalve that is disposed within the release hole and formed by filling the reservoir with a photosensitive hydrogel, exposing the release hole to ultraviolet radiation to cure photosensitive hydrogel disposed within the release hole, and withdrawing uncured photosensitive hydrogel from the reservoir. The photosensitive hydrogel may include, but is not limited to poly(N-isopropylacrylamide), poly(N,N-dimethylacrylamide-co-N-phenylacrylamide), and poly(glycidyl methacrylate-co-N-isopropylacrylamide). The hydrogel microvalve may be self-aligned to the release hole.

The microfluidic device also includes a resonant heater, such as a planar resonant heater, in thermal communication with the hydrogel microvalve is configured to actuate the hydrogel microvalve by heating the hydrogel microvalve. The resonant heater absorbs alternating current electromagnetic energy only at a predefined resonance (also referred to herein as a resonance peak or resonant peak). The predefined resonance can be characterized by a center frequency, which may be from about 1 MHz to about 1 GHZ (e.g., 10 MHz to about 200 MHz), and an active width, which may be about 1 kHz to about 10 MHz (e.g., about 100 kHz to about 5 MHz). Irradiating the resonant heater at the resonance causes the resonant heater to increase in temperature, which, in turn, causes the hydrogel microvalve to deform so as to allow fluid to exit the reservoir.

In an alternative microfluidic device, the release hole is a first release hole, the hydrogel microvalve is a first hydrogel microvalve, and the resonant heater is a first resonant heater configured to absorb electromagnetic energy at a first resonant frequency so as to actuate the first hydrogel microvalve. Such an alternative microfluidic device further includes a second release hole formed in the reservoir and a second hydrogel microvalve disposed with the second release hole to prevent the substance from transiting the second release hole. The alternative microfluidic device also includes a second resonant heater configured to absorb electromagnetic energy at a second resonance frequency so as to actuate the second hydrogel microvalve.

Another embodiment of the present technology is a method of fabricating a hydrogel microvalve. The method begins by filling a reservoir having first and second release holes with a photosensitive hydrogel, such as poly(N-isopropylacrylamide), poly(N,N-dimethylacrylamide-co-N-phenylacrylamide), or poly(glycidyl methacrylate-co-N-isopropylacrylamide). It continues with exposing the first release hole to ultraviolet radiation to cure photosensitive hydrogel disposed within the first release hole. In some cases, exposing the first release hole to ultraviolet radiation may optionally include adjusting the exposure time or exposure intensity to control dimensions of the hydrogel microvalve. Next, the method involves withdrawing uncured photosensitive hydrogel from the reservoir via the second release hole to form the cured photosensitive hydrogel in the first release hole into a hydrogel microvalve.

Optionally, the reservoir's interior surface may be formed of or coated with polyimide, and the interior surface may be treated with an oxygen plasma before filling the reservoir with the photosensitive hydrogel to prevent adhesion of the photosensitive hydrogel to the interior surface. The method may also, optionally, include forming or placing a resonant heater in thermal communication with the hydrogel microvalve. The resonant heater may be configured to absorb alternating current electromagnetic energy only at a predefined resonance.

Still another embodiment of the present technology includes a microsyringe and method of using a microsyringe. One illustrative microsyringe includes a reservoir configured to hold a fluid (e.g., about 5 μL to about 50 μL of a drug or other liquid), a shape-memory alloy (SMA) member having a relaxed state and an actuated state, and a resonant heater in thermal communication with the SMA member. The resonant heater is configured to absorb electromagnetic energy at a resonance so as to actuate the SMA member from its relaxed state to its actuated state, thereby ejecting or releasing at least some of the fluid from the reservoir.

In one illustrative microsyringe, when actuated, at least part of the SMA member may squeeze the reservoir so as to eject fluid. Actuating the SMA member from its relaxed state to its actuated state may result in ejection of a predefined amount of fluid from the reservoir. For instance, actuating the SMA member may result in ejection of about 1 μL to about 5 μL of fluid from the reservoir.

In another illustrative microsyringe, the SMA member is a first SMA member, the resonant heater is a first resonant heater, and the resonance is a first resonance. The other illustrative microsyringe further includes a second SMA member having a respective relaxed state and a respective actuated state and a second resonant heater in thermal communication with the second SMA member. The second resonant heater is configured to absorb electromagnetic energy at a second resonance so as to actuate the second SMA member from its respective relaxed state to its respective actuated state, thereby ejecting additional fluid from the reservoir. In at least one instance, the first resonant heater absorbs electromagnetic energy only at the first resonance and the second resonant heater absorbs electromagnetic energy only at the second resonance, which may have a center frequency of about 1 MHz to about 50 MHz smaller than that of the first resonance.

Yet another embodiment of the present technology includes a method of fabricating a microsyringe. Such a method begins with deposition of a resonant structure on a surface of a substrate and formation of a reservoir on or in the substrate. Next, an SMA member is bonded to the surface of the substrate such that, when actuated, the SMA member causes ejection of fluid from the reservoir. The method also includes providing a thermal conduit from the resonant structure to the SMA.

A further embodiment of the present technology includes a wireless resonant actuator and corresponding method of wireless resonant actuation. The wireless resonant actuator includes plurality of SMA members, each of which has a respective relaxed state and a respective actuated state. For example, the plurality of SMA members may include a first SMA member which, in its respective relaxed state, is in contact with a second SMA member in the plurality of SMA members, and which, in its respective actuated state, is separated from the second SMA member.

The wireless resonant actuator also includes a plurality of resonant heaters, each of which is in thermal communication with a corresponding SMA member. Each resonant heater is configured to absorb electromagnetic energy at a respective resonance so as to actuate the corresponding SMA member from its respective relaxed state to its respective actuated state. For instance, each resonant heater in the plurality of resonant heaters may be configured to absorb electromagnetic energy only at its respective resonance. Each resonant heater in the plurality of resonant heaters may have a resonance whose center frequency that is about 1 MHz to about 50 MHz greater or smaller than the center frequency of the resonance of every other resonant heater in the plurality of resonant heaters.

A still further embodiment of the present technology includes a method of fabricating a wireless thermoresponsive microactuator. The method includes depositing a resonant structure on a surface of a substrate, such as polyimide, glass, ceramic, parylene, or another suitable dielectric. Next, a piece of SMA is bonded to the surface of the substrate, e.g., by electroplating the surface and/or the SMA or by bonding the SMA to the substrate with polymer adhesives. The SMA may optionally be patterned into a member that actuates in response to absorption of alternating-current magnetic energy by the resonant structure, e.g., using micro-electro discharge machining.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the present technology and together with the description serve to explain principles of the present technology.

DETAILED DESCRIPTION

Part I: Thermoresponsive Hydrogel Microvalve Devices

Figure 1:
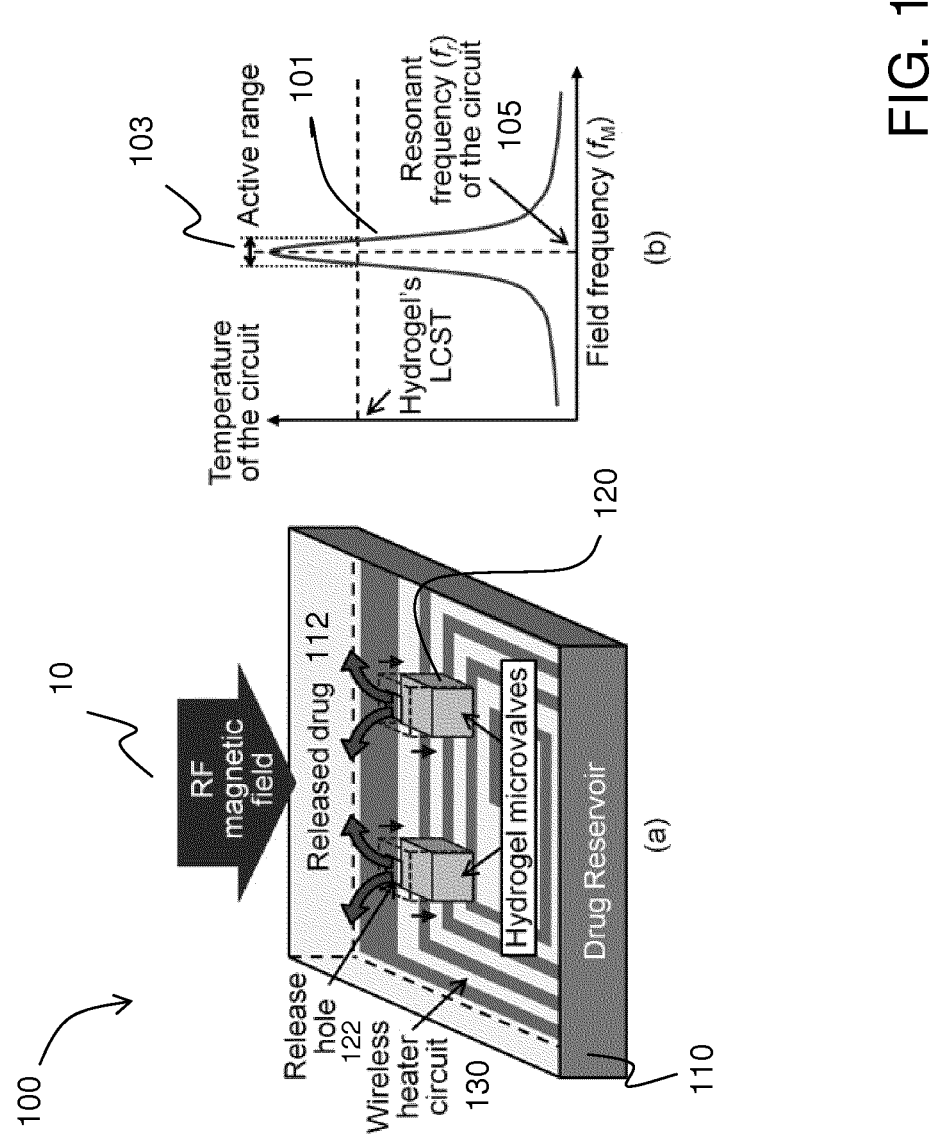
FIG. 1 illustrates (a) an example of a drug delivery device with frequency-controlled wireless heater circuits and hydrogel microvalves and (b) a plot of heater circuit temperature versus field frequency that shows the resonance of the hydrogel microvalves in (a).

Embodiments of the present technology include a micromachined drug delivery device 100 that is operated wirelessly using a radio-frequency magnetic field 10 for implant applications as illustrated in FIG. 1(a). The drug delivery device 100 includes one or more microvalves 120 made of thermoresponsive hydrogel that control the release of drugs 112 from a drug reservoir 110 in the device 100. Suitable hydrogels include, but are not limited to, e.g., poly(N-isopropylacrylamide), poly(N,N-dimethylacrylamide-co-N-phenylacrylamide), poly(glycidyl methacrylate-co-N-isopropylacrylamide), any other suitable thermoresponsive hydrogel, or combinations thereof. In illustrative embodiments, devices may be used to selectively release one or more drugs or other fluids, e.g., with multiple microvalves and reservoirs. Drugs include, but are not limited to, e.g., compositions including peptides, polypeptides, sugars, proteins, lipids, glycolipids, plasmids, cells, insulin, and/or combinations thereof.

At least one microvalve 120 is thermally coupled to a wireless resonant heater circuit 130 in the drug delivery device 100. The wireless resonant heater circuit 130 absorbs energy from the magnetic field 10 at a resonance 101 (plotted in FIG. 1(*b*)), which causes the temperature of the heater circuit 130. The resonance 101, which is shown in FIG. 1(*b*) as heater circuit temperature versus field frequency $f_M$, is characterized by a center frequency 105, also called a resonant frequency $f_R$, and an active width 103. When the field frequency is about equal to the resonant frequency 105 (i.e., when the field frequency falls within the active width 103), the heater circuit temperature rises above the lower critical solution temperature (LCST) of the hydrogel microvalve 120. This increase in temperature actuates the microvalve 120, releasing drug 112 from the drug reservoir via a release hole 122 that is otherwise plugged by the microvalve 120. The active width 103 may span a range of about 100 kHz, 250 kHz, 500 kHz, 1 MHz, 2 MHz, 5 MHz, 10 MHz, or any other suitable bandwidth. Similarly, the center frequency 105 may be in range that includes, but is not limited to, e.g., about 10 MHz and about 200 MHz, between about 50 MHz and about 150 MHz, between about 80 MHz and about 140 MHz, e.g., 100 MHz, 110, MHz, 120 MHz, or any other suitable value.

In addition, forced drug release may be realized by combining micropumps, such as the microsyringes described below, that are thermally operated using a wireless heater in synchronization with thermoresponsive hydrogel microvalves. In some devices, substances within the reservoir may be in powdered or particulate (e.g., nanoparticle) form, and fluid may be circulated through the chamber to flow the powder or particulates out of the chamber.

Figure 2:
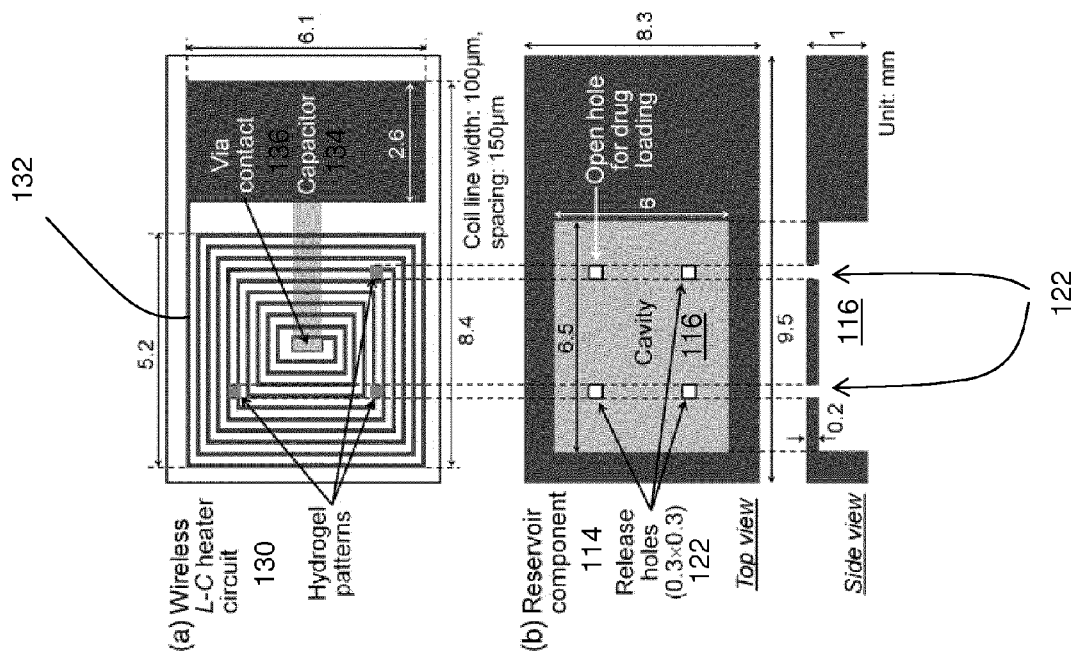
FIG. 2 shows (a) a sample layout of an illustrative wireless resonant heater circuit and (b) top and side views of the design of an illustrative drug reservoir component for the circuit.

FIG. 2 shows how the device 100 shown in FIG. 1(*a*) can be constructed by bonding a 1 mm thick polyimide reservoir component 114 with a reservoir cavity 116 to the heater circuit 130 with a 5-10 mm planar coil 132 fabricated on polyimide film. A via contact 136 couples a capacitor 134 to the planar coil 132. When assembled, the reservoir component 114 and heater circuit 130 from a device 100 whose outer surfaces are polyimide with release holes 122 that provide a conduit through a wall of the reservoir component 113 to the reservoir cavity 116. The release holes 122 in the reservoir component 114 wall are opened and closed by hydrogel microvalves 120 (shown in FIG. 1(*a*)) that are formed inside the reservoir 110 by in situ photolithography that uses the reservoir wall as a photomask, and providing the hydrogel structures self-aligned to the release holes 122.

The wireless heater 110 exhibits fast and strong response to an incident magnetic field 10 at the resonant frequency, with a temperature increase of up to 20° C. for the heater 130. For instance, a heater 130 with a resonant frequency of 34 MHz may, when excited at resonance, heat the hydrogel microvalve 120 so as to shrink the hydrogel by 5%, 10%, 25%, 38%, 40%, 50%, or other suitable value. An active frequency range (active width) of about 100 kHz, 250 kHz, 500 kHz, 1 MHz, 2 MHz, or 4 MHz may be observed for hydrogel actuation. Detailed characteristics of the fabrication and actuation of the hydrogel microvalves 120 as well as experimental demonstrations of frequency-controlled temporal release are provided herein.

Those of skill in the art will readily appreciate that all the specific dimensions and shapes disclosed herein are purely illustrative, and devices falling with the scope of the disclosure may be made in any suitable size and/or shape. For example, the coil 132 may be larger or smaller; the polyimide may be thicker or thinner; and the release holes 122 may be any suitable shape and/or size, e.g., circular, square, rectangular, etc. Further, illustrative devices 100 may include more or fewer members, microvalves 120, release holes 122, and/or reservoirs 110, and such members, microvalves 120, release holes 122, and/or reservoirs 110 may be identical to, or different from, similar components of the same device 100. Similarly, illustrative thermoresponsive actuators and valves may be fabricated using any suitable thermoresponsive material, including, but not limited to, e.g., shape memory alloys, shape memory polymers, hydrogels, bimorphs, paraffin wax, or combinations thereof.

Hydrogel Microvalve Device Operation and Design

Illustrative devices disclosed herein utilize frequency-dependent induction heating to control the actuation of thermoresponsive materials and structures. When an inductor-capacitor (L–C) resonant circuit is exposed to an AC magnetic field, AC current is generated due to electromotive force induced by the field. The power consumed in the circuit, P, can be expressed as:

$$P(\omega) = \frac{Rv^2}{[R + j(\omega L - 1/\omega C)]^2} \tag{1}$$

where v is the electromotive force, L and C are respectively the inductance and the capacitance of the circuit, R is the parasitic resistance of the circuit, and w is the angular frequency of the AC current. The power is maximized when the field frequency, $2\pi f_M$, is identical to the resonant frequency of the circuit, $\omega_r = 2\pi f_r = 1/\sqrt{LC}$, as the reactance becomes zero under this condition, resulting in $P(\omega_r) = v^2/R$. Therefore, the field energy is effectively converted to Joule heat when the frequency of the field matches the resonant frequency of the L–C circuit (i.e., $f_M = f_r$). The steady state temperature rise in the L-C circuit, $T_{SS}$, can be theoretically expressed as:

$$T_{SS} = \frac{R_T v^2 / R}{1 + \alpha_R R_T v^2 / R} \tag{2}$$

where $R_T$ is the thermal resistance to the surrounding of the circuit and $\alpha_R$ is the temperature coefficient resistance of the circuit. The circuit functions as a wirelessly controllable heater that can be actuated (e.g., switched on or off) simply by tuning the field frequency, rather than the field intensity. This mechanism provides an accurate and reliable control for micromachined thermal actuators. In particular, it offers an opportunity to implement selective operation of multiple microactuators using the resonant circuits with different resonant frequency $f_r$ values. This functionality may be leveraged in implantable drug delivery devices for controlled delivery of multiple drugs from partitioned reservoirs. Another important feature is that the field strength necessary to produce a certain amount of heat is much less than that required in non-resonant induction heating. This feature is favorable in terms of achieving reduced doses of electromagnetic radiation to the body.

The wireless actuation principle above can be applied to different types of temperature-sensitive elements such as hydrogels (e.g., poly(N-isopropylacrylamide) (PNIPAM)), shape memory alloys, shape memory polymers, bimorphs, or any other material that changes shape, size, and/or position in response to a change in temperature. This effort particularly targets microvalves that wirelessly regulate the release of drugs or other fluids stored in the reservoirs of implanted devices. Other applications include chemical analysis (e.g., as part of a lab on a chip); use in active catheters, endoscopes, or needles; or any other microfluidic application.

Hydrogel microstructures can serve as soft valves that are expected to achieve more robust sealing compared with harder materials, such as, but not limited to, e.g., metal or plastic. Hydrogels exhibit a phase transition temperature called the lower critical solution temperature (LCST) above which they shrink and deswell the fluid. The LCST value can be modified using different material compositions of the hydrogel, and may be from about 35° C. to about 45° C. in PNIPAMs.

In one illustrative embodiment, PNIPAM hydrogel was selected as the material to form thermoresponsive microvalves. The microvalves are combined with the L–C resonant heater for their actuation in order to control drug release through micromachined holes created in a reservoir wall (e.g., as in FIG. 1(a)). A device was constructed so that a temperature rise above the LCST occurs only when $f_M$ is aligned to $f_r$ of the heater for frequency-controlled actuation of the microvalves (e.g., as in FIG. 1(b)). In some embodiments, a photosensitive PNIPAM is used to lithographically form the microvalve structures on the heater circuit. To initiate drug release, the temperature is brought above the LCST by activating the wireless heater through the field-frequency tuning method; this causes the shrinkage of the hydrogel microvalves, which unplug the release holes through which the drug diffuses out from the reservoir. The generated heat also may contribute to enhancing the diffusion of the drug. Shifting $f_M$ away from $f_r$ deactivates the heater and the microvalve, closing the release holes and terminating the drug release.

Various devices were designed to have spiral coils with overall sizes of 5-10 mm and resonant frequencies of 10-100 MHz. For example, FIG. 2(a) shows a sample design of the wireless L-C heater circuit that has a 6×5 mm$^2$ coil with a theoretical $f_r$ of 94 MHz. In some embodiments, the heater circuits are fabricated on polyimide film using a planar microfabrication process. The drug reservoir is created by bonding a thick polyimide component that has a reservoir cavity (e.g., the cavity 116 shown in FIG. 2(b)) to the planar heater circuit, forming an enclosed reservoir of which an inner surface may be occupied by the spiral coil of the heater when bonded. Prior to the bonding, release holes are created in the thinned wall of the cavity component. This thin wall with the release holes is used as a photomask to implement selective polymerization of the PNIPAM solution injected into the reservoir. This process forms well-defined hydrogel microvalve structures that are self-aligned to the release holes. It also yields a device whose outer surfaces are polyimide or another biocompatible material appropriate for in-vivo applications.

After fabrication, in some embodiments a liquid-phase drug is provided to the reservoir through one of the holes reserved for this filling, followed by sealing this hole. Illustrative devices may also be at least partially filled with drugs and/or other substances in the form of gels, viscous fluids, powder(s), and/or combinations of the same. An optional micropump inside or outside the reservoir may be used to push (viscous) liquid out. For example, a micropump may force fluid into the reservoir through a first actuated microvalve and out through a second actuated microvalve. Alternatively, the liquid or other compound may diffuse out of the reservoir.

Illustrative devices may also be formed with just a single hole instead of at least two holes. The reservoir may be filled with uncured hydrogel via the single hole before being cured, e.g., by exposure to UV light. The cured hydrogel, which seals the hole in its unactuated state, is then actuated to create a gap or opening through the uncured hydrogel is removed from the reservoir. Fluids or powders may be deposited in the reservoir through the same gap. Alternatively, the material to be released from the reservoir may be coated onto the inner surface of the reservoir before the microvalve is formed.

Hydrogel Valve Fabrication

Figure 3:
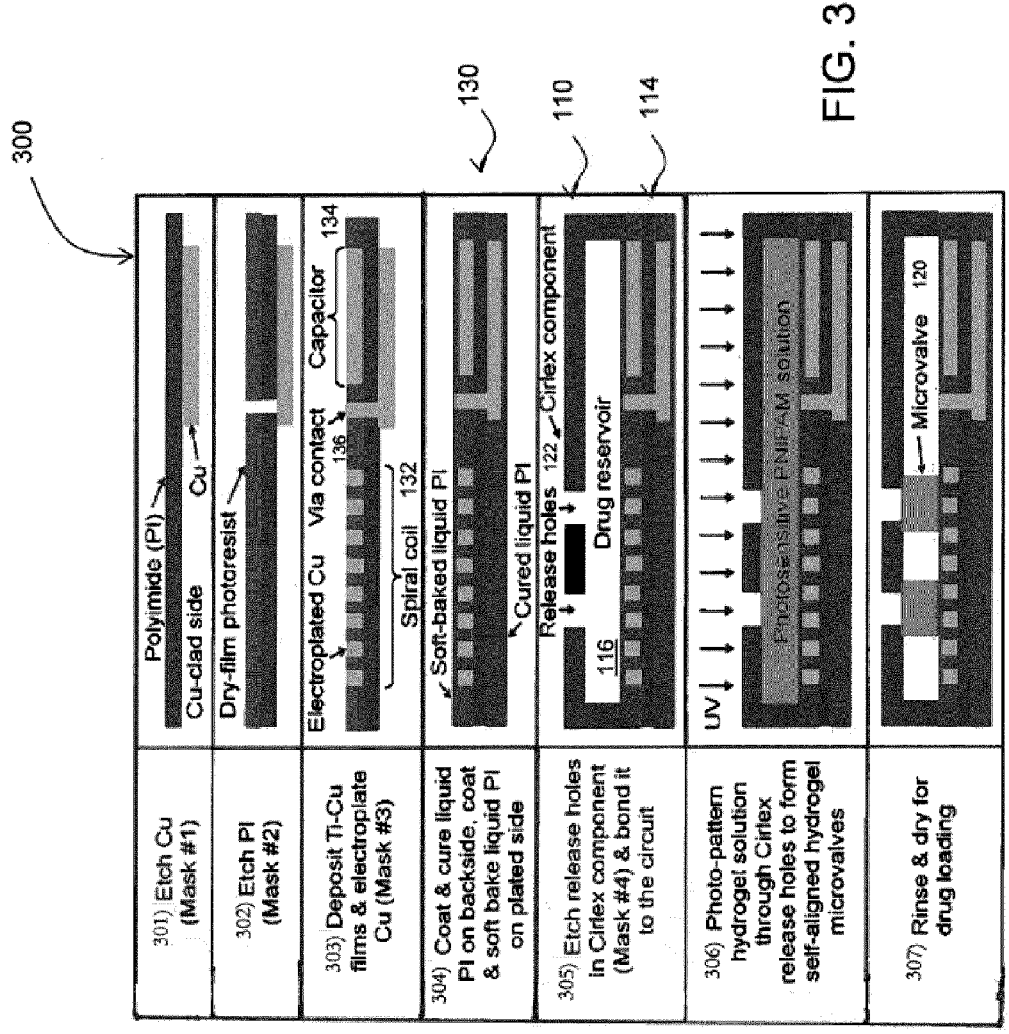
FIG. 3 is a cross-sectional view of a fabrication process for illustrative drug delivery devices.
Figure 4:
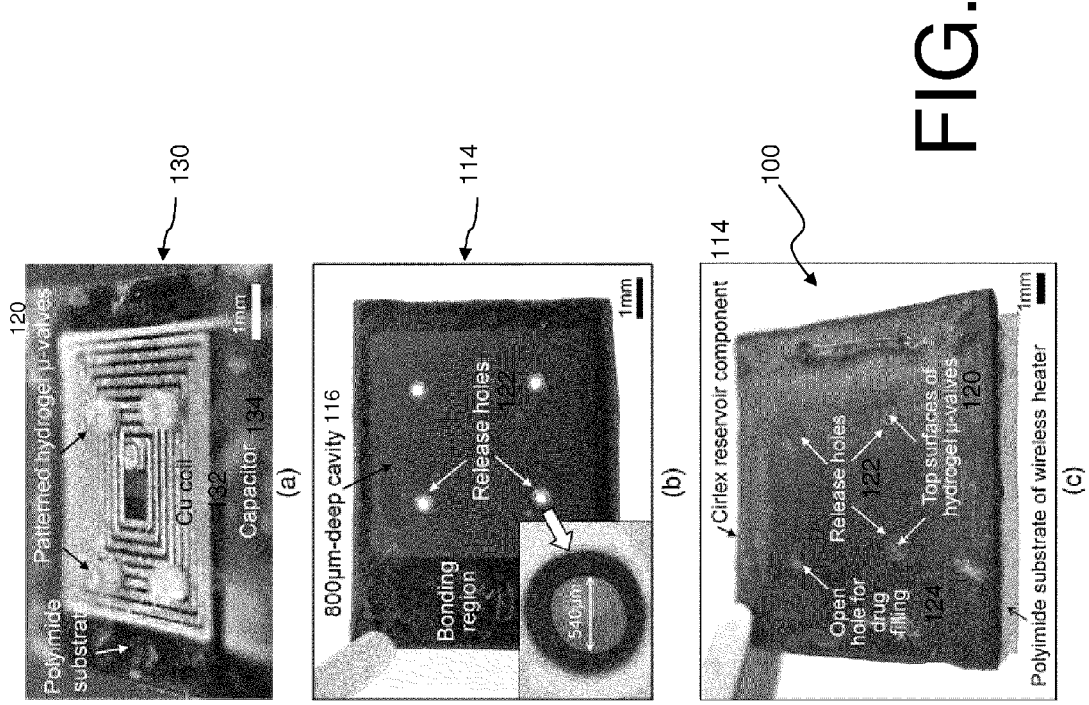
FIG. 4 shows: (a) a fabricated sample L-C heater circuit with photo-patterned poly(N-isopropylacrylamide) (PNIPAM) microvalve structures; (b) a Cirlex® reservoir component with the cavity and release holes (the inset image shows a close-up of one of the release holes created by wet etching); and (c) a fabricated wireless drug delivery device with PNIPAM microvalves formed inside the reservoir, which has release holes plugged by the microvalves.

FIG. 3 illustrates an illustrative fabrication process 300 developed for making the device 100 shown in FIGS. 1 and 2. The planar L-C heater circuit 130 is fabricated on single-sided copper-clad polyimide film with 50 μm thickness (G2300, Sheldahl Co., MN, USA). Dry-film photoresists (38 μm thick DuPont PM240 and 15 μm thick MacDermid LF106) can be used for all patterning processes. First, wet etching of the copper-clad layer is performed to form the back plates of the capacitor 134 using patterned LF106 as a mask (FIG. 3, step 301). Next, via contacts 136 that connect the planar coils 132 to be formed on the polyimide side to the back plates of the capacitor 134 are created in the polyimide film by wet etching in a potassium hydroxide (KOH) based solution (40 wt. % KOH and 20 wt. % ethanolamine in de-ionized (DI) water) at 87° C. using a patterned PM240 mask (FIG. 3, step 302). After depositing a titanium-copper thin-film seed layer on the polyimide side of the film, a PM240 mold is patterned on top of the layer to perform copper electroplating of the planar coils 132 and the other capacitor plates for a thickness of 30-35 μm (FIG. 3, step 303). After removing the PM240 mold, the electroplated structures are electrically isolated from each other by wet etching of the seed layer for the portions that are not electroplated. Next, the copper-clad side of the circuits are coated with liquid polyimide (HD-4110, HD Microsystems, NJ, USA) for 20 μm thickness and hard baked (FIG. 3, step 304), forming a physical and electrical protective layer for the heater circuit 130. FIG. 4(a) shows a sample of the planar L-C circuits (with patterned hydrogel structures discussed later) obtained through the above process.

The reservoir component 114 is fabricated using conventional mechanical machining processes in 1 mm thick Cirlex® polyimide sheets (Fralock Inc., CA, USA) (FIG. 4(b)). The thickness of the thinned wall of the machined cavity 116 is approximately 200 μm. The release holes 122 are created in the thinned wall by wet etching from the opposite side of the cavity 116 using a photoresist mask and the same KOH etchant used to form the via contacts in the polyimide film. Prior to etching, the cavity side of the reservoir component 114 is also coated with a photoresist for protection. The etch rate of Cirlex® in the etchant is approximately 4.4 μm/min. Release holes 122 designed to have square shapes in the mask as shown in FIG. 2(b) tend to result in circular shapes after etching (e.g., as shown in FIG. 4(b)) due to the isotropic nature of the process. For example, 300 μm square patterns on the mask form tapered holes with an average diameter of about 700 μm on the top side of the 200 μm thick wall and about 500 μm on the backside of the wall after 1-hour etch, resulting in sidewall angles of about 60°. A polyimide-topolyimide solvent bonding technique is utilized to achieve uniform, leak-free bonding between the Cirlex® cavity components and the heater circuits. The bonding process starts with spin coating of the liquid polyimide on the circuit, followed by soft baking on a hotplate at 90° C. for 5 minutes. N-methyl-2-pyrrolidone, a polyimide solvent, is applied to the bonding regions of the Cirlex® component, which is then placed on the circuit. The combination is hard baked at 100° C. on a hotplate while applying a pressure (e.g., about 30 KPa) for 25 minutes (FIG. 3, step 305).

In some embodiments, the synthesis of the photosensitive PNIPAM solution uses a 2% cross linking formula. For hydrogel microvalve formation, first, the reservoir 110 created by the bonding process is filled with the synthesized hydrogel solution through one 124 of the release holes 122 using a needle syringe. All the holes 122 except at least the hole 124 to be used for drug filling are then exposed to ultraviolet (UV) light with 400-nm wavelength at 8.6 mW/cm$^2$ (FIG. 3, step 306). The optical transmission in Kapton® is nearly zero below 500-nm wavelength. Since the Cirlex® is thick Kapton®, the local polymerization occurs only below the release holes, forming well-defined hydrogel columns or microvalve structures 120 inside the enclosed reservoir space (FIG. 4(a)). Using this in situ photolithography with proper conditions, the bottoms of the columns adhere to the cured liquid-polyimide surfaces of the circuit while the tops of the columns touch the inner surfaces of the Cirlex® cavity around the holes 122. It was observed that the hydrogel had a good adhesion to the circuit. This adhesion could be exploited to create a chemically activated, permanent "off" switch for the microvalve 120: exposing the hydrogel microvalve and/or the release hole surface to an adhesion promoter may cause the hydrogel to permanently adhere to the release hole, thereby preventing further actuation of the microvalve.

During device operation, adhesion between the hydrogel and the Cirlex® surfaces around the release hole 122 is undesired due to the risk that adhesion may cause the hydrogel microvalve 120 to plug the hole 122 even when the hydrogel microvalve 120 is actuated. Oxygen plasma treatment was observed to be effective in preventing this adhesion and allowing drug release upon hydrogel actuation. Thus, the cavity surfaces of the Cirlex® components were processed with oxygen plasma (5 minutes at 300 W) prior to the bonding described above. The remaining hydrogel solution that is not polymerized is removed from the reservoir 110 through the open hole 124 using a needle syringe; then the reservoir 110 is thoroughly rinsed by injecting and flowing de-ionized (DI) water in a similar manner (FIG. 3, step 307). FIG. 4(c) shows a fabricated device 100 after step 307. Finally, the reservoir 110 is filled with a selected drug through the open hole 124, which is then sealed using biocompatible adhesive (Kapton® tape was used for experimental testing).

In some embodiments, e.g., for the in situ formation of the microvalves 120 through the polyimide "mask," hydrogel dimensions may be precisely controlled in order to achieve complete normal closure of the release holes. For this purpose, the relationship between the dimensions of photo-patterned microstructures and the UV exposure time was characterized. The dimensions of polymerized structures defined by different exposure times (with a 10-second step) were measured using a Nikon MM-400 optical measuring microscope. The exposure was implemented using the same method and condition (patterning on cured liquid-polyimide surfaces through the release holes of a Cirlex® cavity treated with oxygen plasma) performed in the device fabrication. The opening diameter of the holes created in the 200 μm thick Cirlex® wall and the depth of the cavity were measured to be approximately 630 μm and 795 μm, respectively. After each exposure, the cavity component was removed from the substrate and the polymerized hydrogel structure formed on the substrate was rinsed with de-ionized (DI) water.

Figure 5:
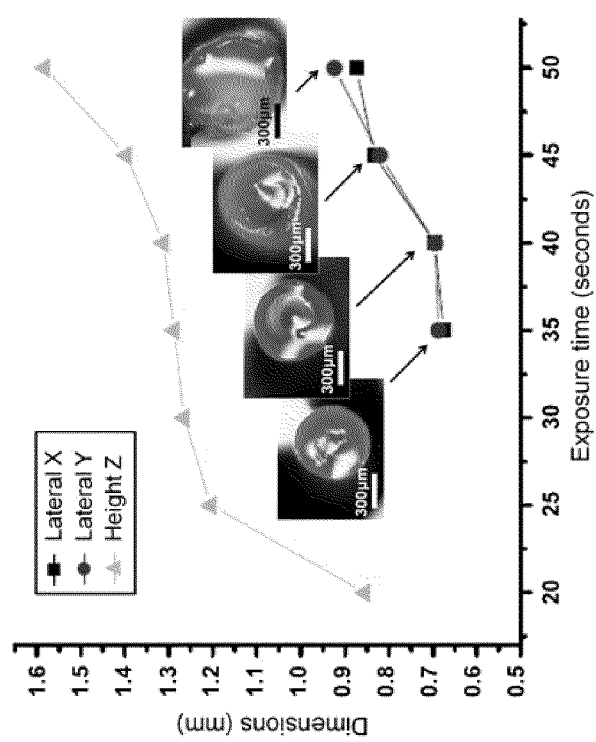
FIG. 5 shows a typical measurement result in dimensional changes of illustrative photo-patterned PNIPAM structures versus ultraviolet (UV) exposure time. The inset images (with an identical magnification) show the top surface of the structures at the corresponding exposure times, indicating lateral extensions of the structures due to longer exposure times.

FIG. 5, which is a plot of microvalve dimension versus exposure time, shows that the measured dimensions were somewhat larger than the cavity height and the size of the hole opening partly due to an uptake of the rinsing water (this effect is discussed below). The inset images show the top of the measured microvalve when each measurement was taken. The minimum time required to achieve the hydrogel height equal to the cavity height was measured to be about 20 seconds while the minimum time to transfer the shape of a release hole to the top portion of the hydrogel was about 35 seconds (therefore the plots in FIG. 5 start from these times). As can be seen in FIG. 5, the hydrogel structures extend in both lateral and vertical directions as the exposure time is increased. This indicates two favorable aspects in the formation of hydrogel microvalves with respect to leak prevention: 1) The cross-sectional areas of the patterned hydrogel columns can be larger than those of the holes, ensuring full coverage the holes; 2) the columns can be grown to be taller (in their free-standing state) than the height of the cavity so that their top portions are pushed against the hole regions to eliminate any gap between the hole and the hydrogel at its normal/inactivated condition. To achieve these two conditions, the exposure time of 45 seconds was used for the hydrogel patterning in the fabrication process.

Exemplification of Hydrogel Microvalve Device

To characterize the behavior of the hydrogel microvalves, the deswelling rate of the photo-patterned PNIPAM hydrogel was measured as a function of temperature. The performance of the device components was evaluated with a wireless set-up, followed by the demonstration of wireless control of temporal release using the fabricated devices.

Thermal Response of Photo-Patterned PNIPAM

In order to achieve proper operation of the hydrogel microvalve actuators, it is important to understand how the polymerized hydrogel swells and de-swells (shrinks) in response to changes of the ambient temperature in detail. For this, first, samples of the PNIPAM structures polymerized by the patterning method previously described were rinsed with DI water and left in air to be dried completely. Next, the samples were immersed into DI water in a dish and left at room temperature until they reached a fully swelled state. The temperature of DI water was then increased step by step on a hotplate while measuring the dimensions of the samples after each temperature was stabilized.

Figure 6:
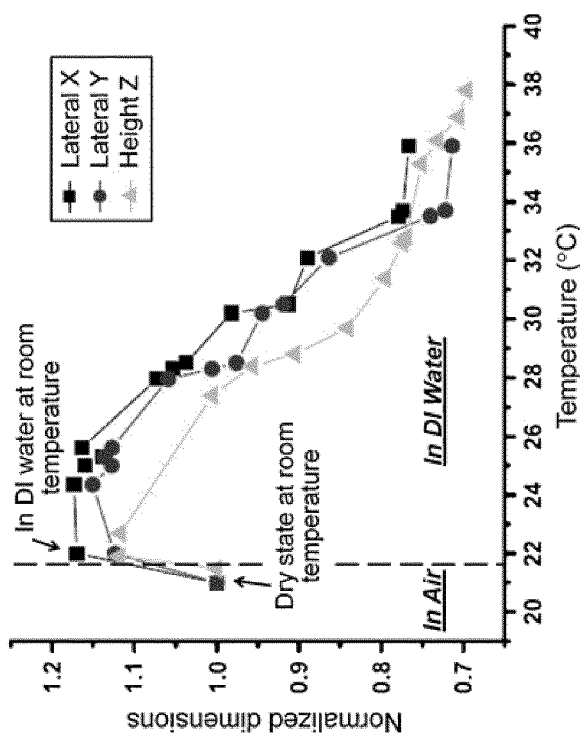
FIG. 6 illustrates measured dimensional changes of an illustrative photo-patterned PNIPAM structure versus temperature. The plots are normalized to the dimensions at the dry state of the structure at room temperature.

FIG. 6 is a plot of the changes in the cross-sectional diameters measured in perpendicular (X/Y) directions and the height (Z) of a typical sample. (The plots are normalized to the dry-state values of X=0.73, Y=0.75 mm, and Z=1.3 mm at room temperature.) The results show a similar trend in all three dimensions, with a 12-17% increase due to the ambient change from air to DI water (i.e., due to absorption of DI water) and a 34-38% reduction due to the temperature change from room temperature to 36° C. in DI water. FIG. 6 also shows that in DI water, the hydrogel shrunk down below its dry-state size when temperature was raised to 28-30° C., which is equal to the LCST of the hydrogel material (in the particular case in FIG. 6, a weak transition at the temperature is seen in the height of the sample) as well as the LCST for this hydrogel reported elsewhere. This suggests that the wireless heater can to provide heat to raise the hydrogel temperature to the above level or more for the designed microvalve operation.

Characterization of Wireless Resonant Heaters

Figure 7:
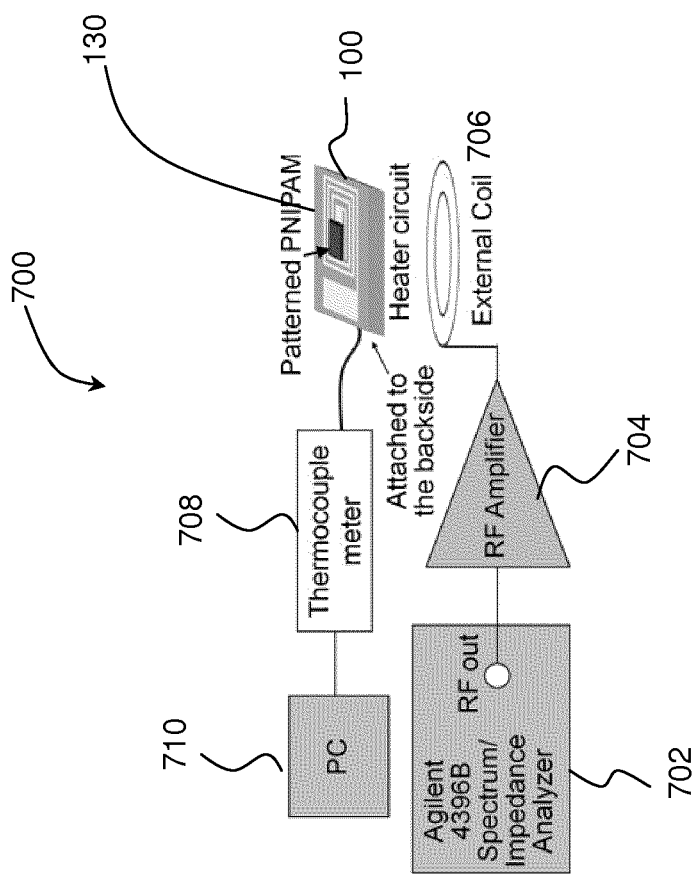
FIG. 7 shows a wireless set-up for the characterization of illustrative resonant heaters and PNIPAM structures.

FIG. 7 shows a set-up 700 for testing drug delivery devices 100 with wireless resonant heaters 130 and hydrogel microvalves 120. A spectrum/impedance analyzer 702 or other synthesizer emits a radio-frequency (rf) signal, which is coupled to an rf amplifier 704 that amplifies the rf signal. The amplified rf signal drives an external coil 706 (40 nH) to generate an AC magnetic field, which was radiated to the heater component 130 above the coil 706. Thermal characterization was performed by a thermocouple 708 that was fixed to the backside of the heater 130 using silicone adhesive. It was verified experimentally that the dependence of thermocouple output on the presence of the field with the power level and frequencies used in the tests was minimal or undetectable. A personal computer (PC) 710 coupled to the thermocouple 708 recorded and processed signals from the thermocouple 708.

Figure 8:
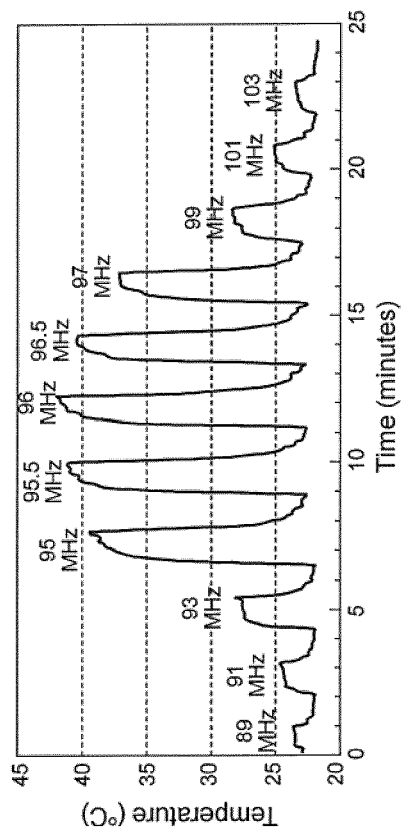
FIG. 8 shows the thermal response of a fabricated resonant heater with a resonant frequency $f_r$=96 MHz to temporal wireless excitation with varying frequencies at a constant excitation power.

FIG. 8 is a plot of the temperature measured by the thermocouple as a function of time, during which the rf signal's center frequency $f_M$ (also referred to as the field or modulation frequency) swept from about 89 MHz to about 103 MHz. The thermal response to periodic excitations with different $f_M$ values was characterized in air using a fabricated heater with a 5 mm sized spiral coil with a measured resonant frequency of $f_r$=96 MHz. FIG. 8 shows that the heater exhibited quick responses in their heat generation to the presence of a field—approximately 80% of the total temperature rise (e.g., 19.2° C. at $f_M$=96 MHz) occurred within fifteen seconds of excitation. It also shows that the highest temperature was achieved when $f_M=f_r$.

Figure 9:
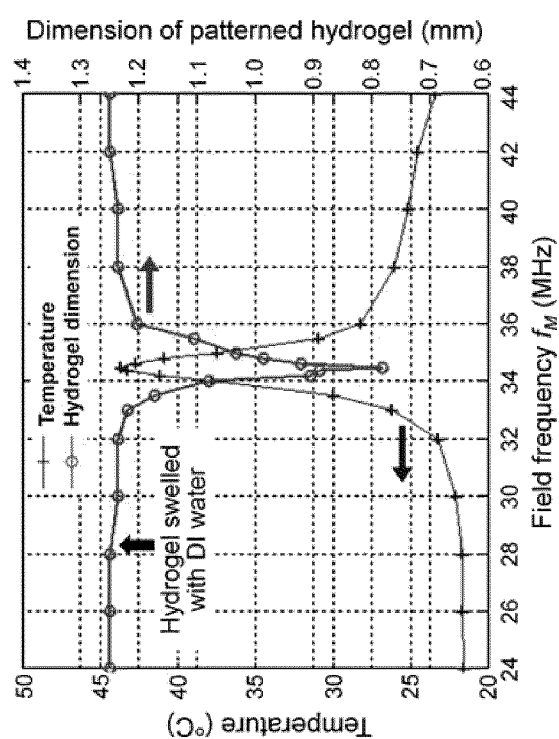
FIG. 9 shows the frequency dependence of the heater temperature and the size of the PNIPAM hydrogel photo-patterned on an illustrative heater.

FIG. 9 is a plot of measured temperature (left axis) and lateral dimension of a fully swelled PNIPAM hydrogel microvalve (right axis) versus field frequency for a heater with a 10 mm sized coil ($f_r$=35 MHz). The temperature peaks strongly at a field frequency roughly equal to the device's resonant frequency, $f_r$. FIG. 9 also shows that the lateral dimension of the microvalve shrunk to 62% of its initial (i.e., swelled) size at the resonance frequency of the heater. The shrinkage occurred when the heater temperature exceeded around 30° C., which is the LCST of PNIPAM as mentioned above. In the above tests, the heater-hydrogel components showed an active frequency range for the hydrogel actuation of approximately ±1 MHz at their resonant frequencies.

Microvalve Release Tests

Figure 10:
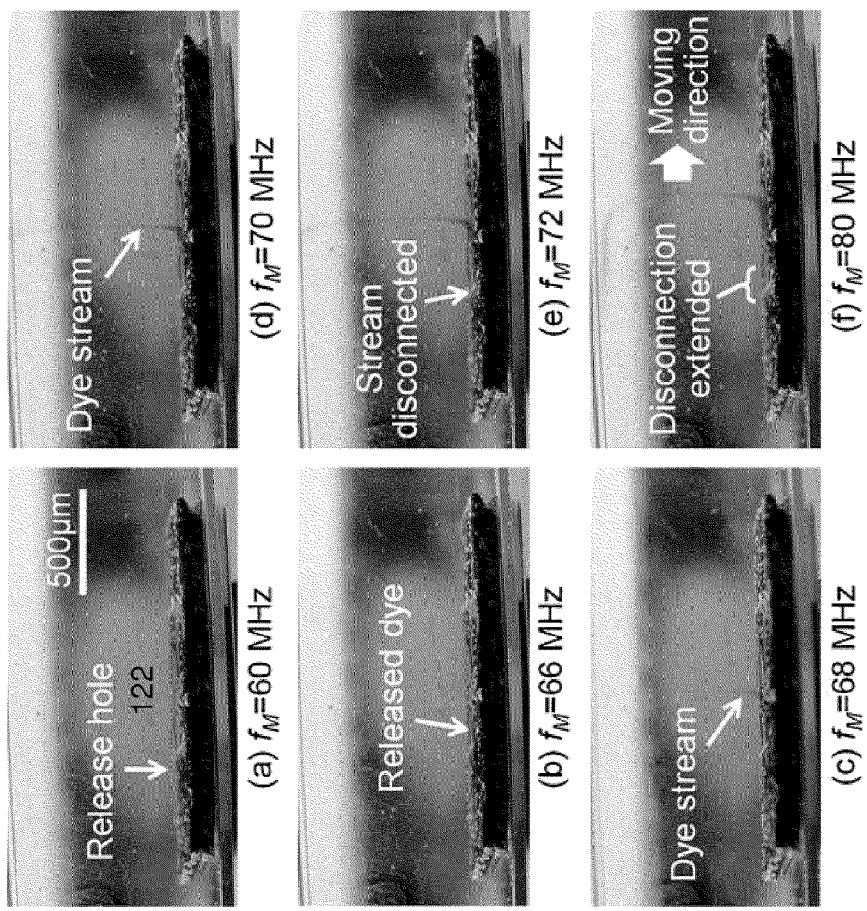
FIG. 10 shows images from the preliminary test for wireless release control through a fabricated device with color dye immersed in DI water. While increasing the modulation frequency $f_M$ from 60 MHz, the dye release was observed to be initiated at about 66 MHz. The dye stream produced was slowly moving laterally due to a convection effect in de-ionized (DI) water. When $f_M$ reached about 72 MHz, a disconnection of the stream appeared, indicating the termination of the dye release.

FIG. 7 illustrates microvalve release tests performed by filling the drug reservoir 110 of a fabricated device 100 with a food-color dye. The device 100 used was measured to have $f_r$=72 MHz in air, and only one of the release holes 122 was used (the other holes were sealed with Kapton® tape). The wireless test set-up used was the same as the set-up 700 of FIG. 7, except that the device 100 was immersed in a dish containing DI water below which the external coil 706 was located. First, a magnetic field at $f_M$=60 MHz with the output RF power of about 800 mW was turned on, and showed no detectable release (FIG. 10(a)). The $f_M$ value was then increased with a 1-MHz step. The dye release started when $f_M$ reached 66 MHz (FIG. 10(b)), and the release continued to increase until $f_M$ reached 70 MHz (FIGS. 10(c) and (d)). As $f_M$ increased to 72 MHz and above, the flow decreased and eventually stopped (FIGS. 10(e) and (f)). This indicates that the hydrogel microvalves properly responded to the frequency tuning for the controlled release. The actual $f_M$ that initiated the release was several megahertz off from the $f_r$ in air, which is likely due to operation in the liquid environment. Changes in environment may be compensated for to allow more precise release control.

Figure 11:
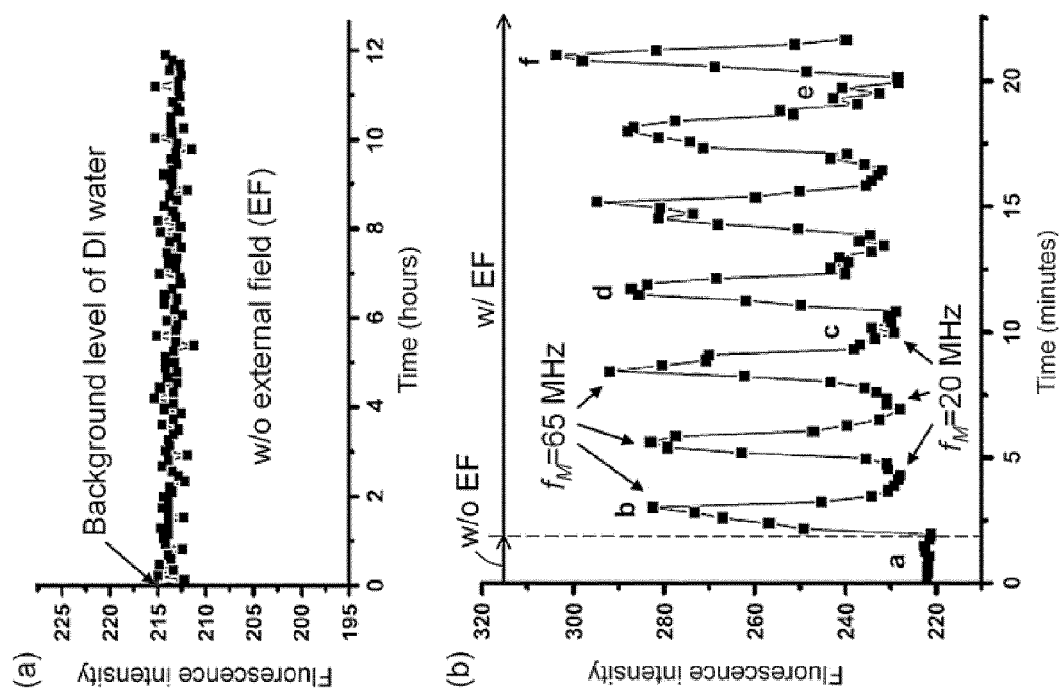
FIG. 11 shows measured fluorescence intensities observed with a fluorescein-loaded device in DI water for: (a) a leak test result measured with no external field and (b) a wireless temporal release control test using frequency tuning techniques (the periodic intensity peaks in (b) are generated by tuning the modulation $f_M$ in and out of resonance and the letters in (b) correspond to the images in FIG. 12).

FIG. 11 illustrates the results of another release test performed using fluorescein, a fluorescent dye (absorption maximum at 494 nm, emission maximum at 521 nm in water), for a device with $f_r$=65 MHz in air. A fluorescent microscope (Eclipse TE2000-U, Nikon Inc., NY, USA) was used to characterize the concentration of fluorescein released from the device. All the measurements were performed in DI water in a dish without agitation or forced flow. Prior to the release test, leak tests were performed. For this, the device fully filled with fluorescein was immersed in DI water (total amount about 7.8 cc) and the fluorescence intensity was measured every seven minutes over twelve hours at a location approximately 400 μm away from one of the release holes while no external field was present. As can be seen in the measurement result in FIG. 11(a), which is a plot of detected fluorescence intensity versus time, no distinct increase of the intensity was detected for the entire twelve-hour test period. In fact, the fluorescence intensity level observed in this leak test was almost identical to the background level measured with fresh DI water (corresponding to the first dot at the time of zero) before immersing the device.

The release test was conducted as follows: After leaving the device in DI water with no external field for two minutes, an external field at $f_M$=65 MHz was turned on for about 1 minute, then $f_M$ was shifted and kept at 20 MHz for about two minutes; this $f_M$ cycle of tuning in and out of 65 MHz was repeated while measuring the intensity with the same method used in the leak test. The RF output power was kept constant (at about 800 mW) during the entire period that the external field was present.

FIG. 11(b) shows the measured fluorescence intensity versus time for the fluorescein release test. In the graph, the initial flat region (labeled "a") corresponds to a period without any externally applied electromagnetic field. The flat region is followed by periodic peaks (e.g., "b," "d," and "f") that appeared when $f_M$ was tuned to 65 MHz. As $f_M$ was shifted to 20 MHz, the intensity dropped and returned to the base value (e.g., at "c"). This decrease of intensity or dye concentration is apparently because once the dye release was terminated, the released dye present at the measurement location quickly diffused away from the location. FIG. 11(b) also shows that the average intensity during the test slightly increased as the cycle was repeated. This small increase was most likely due to the accumulation of the released dye in a dish.

Figure 12:
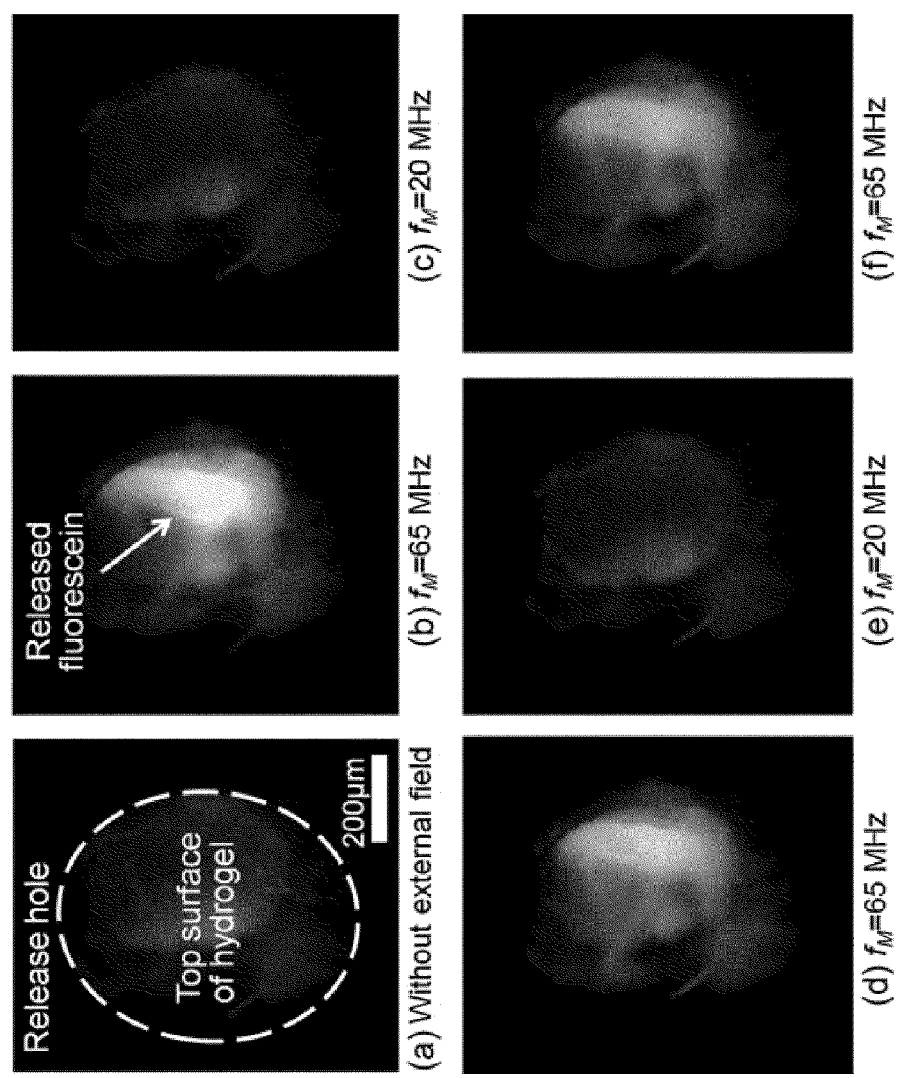
FIG. 12 shows images of the release hole (with an angled view) captured during the temporal release test shown in FIG. 11(b) using the fluorescent microscope, demonstrating dye release (in the bright regions in (b), (d), and (f)) in response to resonant field frequency tuning (the letters correspond to points indicated in FIG. 11(b)).

FIG. 12 shows fluorescence images of the release hole used for the measurement (the captured timings (a) through (f) correspond to the labels in FIG. 11). The bright regions in FIGS. 11(b), (d) and (f) represent dye that diffused out of the reservoir though a gap created between the release hole and the hydrogel microvalve when the microvalve was actuated by the resonating heater (i.e., when the external field frequency equaled the resonant frequency, $f_M=f_r$=65 MHz). In FIGS. 11(c) and (e), the bright region disappeared as shifting $f_M$ to 20 MHz caused a temperature drop that led to swelling of the hydrogel microvalves, closing off the release hole and terminating the dye release.

Part II: Shape Memory Alloy-Based Microactuators

Further embodiments of the present technology include bulk-micromachined shape-memory material (SMM) actuators, including but not limited to, e.g., microgrippers, microsyringes (which could be used as micropumps), micropumps, catheters, endoscopes, guided needles, or any other device that can be deformed (bent), pushed, or pulled into a desired position and/or shape, that can be controlled wirelessly using external radiofrequency magnetic fields. Suitable shape-memory materials include shape-memory alloys (SMAs) and shape-memory polymers (SMPs). Suitable SMAs include, but are not limited to, e.g., nickel-titanium (nitinol), copper-aluminum-nickel, and copper-zinc-aluminum-nickel. Suitable SMPs include, but are not limited to, e.g., thermoset and thermoplastic (covalently cross-linked) polymers. Although the devices described herein were fabricated using SMA with an austenite-phase temperature of 65° C., other SMMs with different austenite-phase temperatures can be used to achieve a different actuation temperature of the device.

FIG. 13(a) shows an illustrative microgripper device 1300 that includes a gripper 1322 in thermal communication with a resonant LC heater circuit 1330. The gripper 1322, which is made of an SMM, such as an SMA, features a pair of cantilever members 1320a and 1320b whose tips are separated from in each when relaxed (as shown in FIG. 13(a)) and come together when the gripper 1322 is heated (as indicated by dashed lines 1320a' and 1320b'). When subject to an rf magnetic field 10 tuned to its resonant frequency, the heater circuit 1330 heats up, causing the cantilever members 1320a and 1320b (collectively, cantilever members 1320) to move from their respective relaxed positions to their respective actuated positions 1320a' and 1320b', respectively. In other words, applying a resonant magnetic field 10 to the heater circuit 1330 causes the gripper 1322 to close, and removing the resonant magnetic field 10 causes the gripper 1322 to open. (Alternatively, the cantilever members 1320 may touch each other when relaxed and be separate from each other when actuated.)

FIG. 13(b) is a plot of heater circuit temperature versus the frequency of the applied rf magnetic field 10. The plot features a resonance 1301 within which the heater circuit 1330 absorbs applied electromagnetic energy. The resonance 1301 can be characterized by its center frequency 1305, also call the resonant or resonance frequency $f_R$ of the heater circuit 1330, and an active width 1303, which is the frequency range over which the temperature of the heater circuit 1330 exceeds the austenite temperature of the gripper SMA. The active width 1303 may be, but is not limited to, e.g., 100 kHz, 250 kHz, 500 kHz, 1 MHz, 2 MHz, 5 MHz, 10 MHz, or any other suitable bandwidth. Similarly, the center frequency 1305 may be between about 10 MHz and about 200 MHz, between about 50 MHz and about 150 MHz, between about 80 MHz and about 140 MHz, e.g., 100 MHz, 110, MHz, 120 MHz, or any other suitable value.

The heater circuit 1330 absorbs electromagnetic energy whose frequency falls within the resonance 1301; electromagnetic energy with a frequency that falls within the active width 1303 of the resonance 1301 can heat the heater circuit temperature above the actuation temperature of the gripper 1322. The peak temperature occurs when the applied rf magnetic field 10 is tuned to the resonant frequency 1305 of the heater circuit 1330. Heating the gripper 1322 above its austenite temperature causes the gripper 1322 to close.

The gripper 1322 is mechanically and thermally coupled to the heater circuit 1330, which is made using copper-clad polyimide film, using a batch-compatible bonding technique based on photo-defined copper electroplating. In some cases, the bond may have a shear strength greater than 40 MPa (e.g., 45 MPa, 50 MPa, 55 MPa, or 60 MPa). In one example, the cantilever members 1320 are about 5 mm long and have a combined actuation range of about 600 µm (i.e., each member 1320 moves about 300 µm). Alternative cantilever members 1320 may longer or shorter (e.g., 1 mm, 2 mm, 3 mm, 4 mm, 6 mm, or 7 mm long) with greater or smaller combined actuation ranges (e.g., 100 µm, 200 µm, 300 µm, 400 µm, 600 µm, 700 µm, or even 1 mm).

The cantilever members 1320, or beams, shown in FIG. 13(a), have identical rectangular cross sections and fabricated so that one of the sidewalls of each of the members 1320 is coated with the cold-state reset layer. Although the gripper 1322 described below includes SMA members 1320 with identical dimensions, those of skill in the art will readily appreciate that other SMA devices, such as grippers, may be made with one or more members of identical or different shapes, sizes, and/or dimensions. For example, a gripper may be fabricated with only a single moving member that closes against a fixed (static) surface. In addition, illustrative grippers and other microactuator devices may fabricated such that their unactuated state is either open or closed as desired.

The gripper 1322 material reaches an austenitic-phase temperature of 65° C. (i.e., its actuation temperature) at a device temperature of 92° C. Those of skill in the art will readily appreciate that austenitic-phase temperature depends on the type of SMM used to make the gripper 1322, and that the device temperature at depends on the geometry and construction of the device 1300. The heater circuit 1330 may have a resonant frequency of 140 MHz or another other suitable value (e.g., any value within a range of about 50 MHz to about 200 MHz) with a resonance width of about 1 MHz to about 20 MHz (e.g., about 13 MHz).

Also disclosed herein is a batch-compatible planar assembly technique based on photo-defined selective electroplating for bonding SMA actuators to heater circuits and/or other devices. Illustrative gripper devices based on the above SMA actuation method with the one-way memory principle are designed and microfabricated using the developed bonding technique and experimentally characterized. The manipulation of vertically aligned carbon-nanotube (CNT) forests is presented as a demonstration of the RF control of the fabricated devices. The mechanical strength provided by the bonding technique is characterized with different sample conditions.

The frequency selectivity of the present technology provides an opportunity to implement simultaneous control of multiple SMA actuators bonded to the wireless heaters with different resonant frequencies. The developed bonding technique based on photo-defined electroplating may be applied to the fabrication of arrayed bulk-SMA microactuators by scaling up the technique, potentially enabling their wafer-level integration. In addition, in order to achieve uniform heating of SMA structures and an improved temporal response, these structures may be integrated with heat sources by, e.g., patterning portions of the wireless heater circuits on the structures, or designing SMA structures to be part of the circuits thus producing Joule heat directly.

Thermal Actuation of Micromachined SMA Devices

In illustrative embodiments, a micromachined SMA actuator 1300 can be operated through an inductor-capacitor (LC) resonant circuit 1330 that serves as a frequency-sensitive wireless heater activated by an external RF magnetic field (e.g., as in FIG. 13(a)). As described above, an AC current is generated in an LC circuit when the circuit 1330 is exposed to an AC magnetic field due to the electromotive force induced by the field. The power consumed in the LC circuit, P, can be expressed as:

$$P(\omega) = \frac{Rv^2}{[R + j(\omega L - 1/\omega C)]^2} \quad (3)$$

where v is the electromotive force, L and C are respectively the inductance and the capacitance of the circuit 1330, R is the parasitic resistance of the circuit 1330, and ω is the angular frequency of the AC current. The reactance in Eq. (3) is eliminated when the frequency of the AC current, or that of the magnetic field, matches the resonant frequency of the circuit 1330, $\omega_r = 1/\sqrt{LC}$. At this condition, the power transfer to the circuit 1330 is maximized, resulting in:

$$P(\omega_r) = \frac{v^2}{R} \quad (4)$$

Thus, the field energy is effectively converted to Joule heat when the field frequency is tuned to the resonant frequency of the LC circuit 1330, i.e., the actuation is controlled with the frequency, rather than the field intensity. The steady state temperature rise of the LC circuit 1330, $T_{ss}$, can be theoretically expressed as:

$$T_{SS} = \frac{R_T v^2 / R}{1 + \alpha_R R_T v^2 / R} \quad (5)$$

where $R_T$ is the thermal resistance to the surrounding of the circuit 1330 and $\alpha_R$ is the temperature coefficient of resistance of the circuit.

Figure 13:
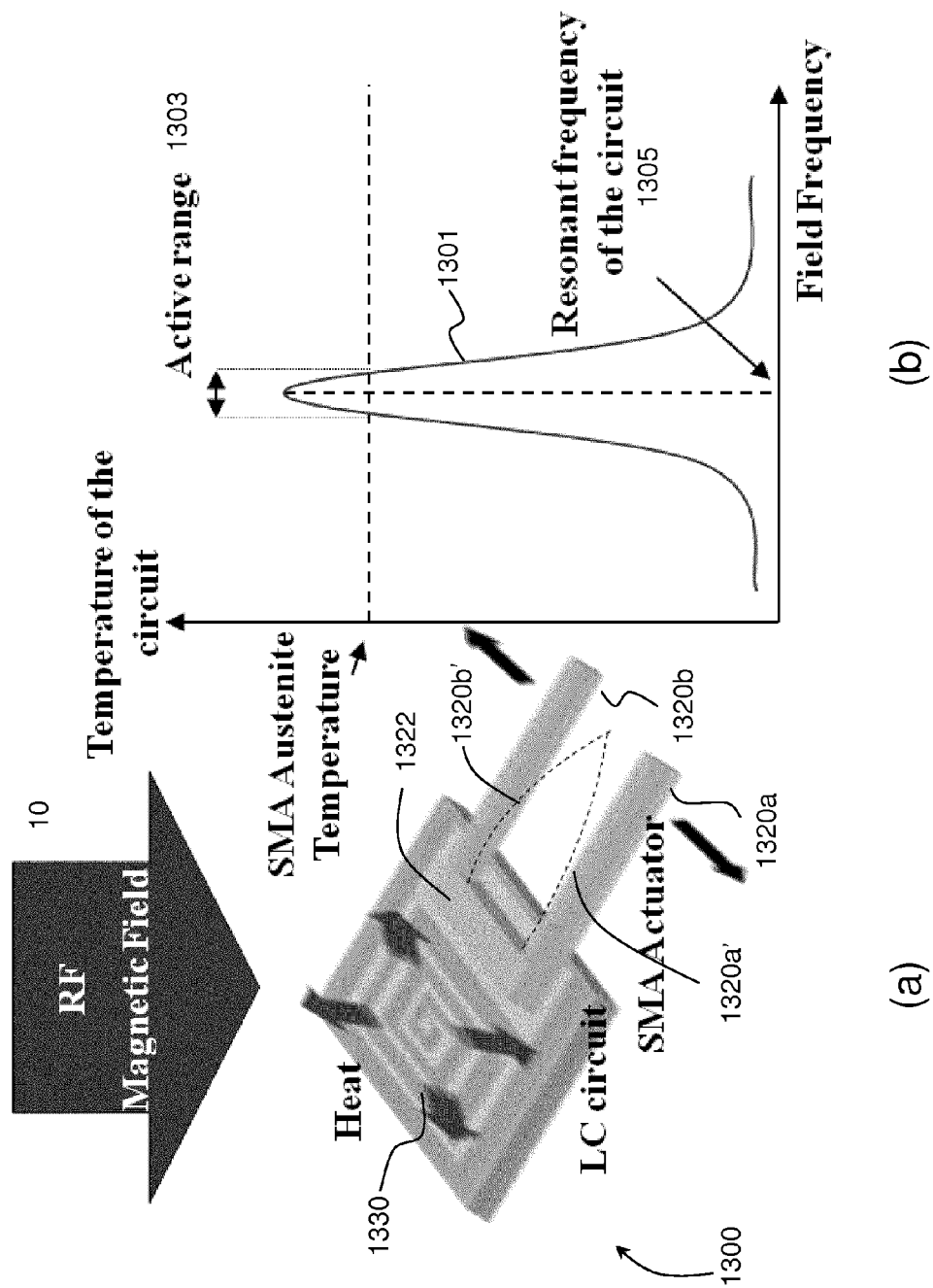
FIG. 13 illustrates (a) an example of a wirelessly controlled shape memory alloy (SMA) microgripper and (b) a plot of SMA austenite temperature versus field frequency that shows the resonance of the heater circuit and the actuation threshold of the microgripper in (a).

When the temperature of the device exceeds the austenite-phase temperature of the SMA, the gripper 1322 is actuated as the material returns to its remembered shape (FIG. 13(*b*)). The shape of the gripper 1322 is restored to be its original cold-state shape when heat is removed due to the force provided by the reset layer. Although the device 1300 shown in FIG. 13(*a*) is fabricated using an SMA with an austenite-phase temperature of 65° C., other SMAs with different austenite-phase temperatures can be used to achieve a different actuation temperature of the device. The electroplating-based bonding (discussed below) is used to achieve not only high-precision assembly of the micromachined SMA gripper 1322 on the wireless heater 1330 with high mechanical bonding strength but also high thermal conductance between the two components.

SMA Gripper Device Design and Fabrication

Figure 14:
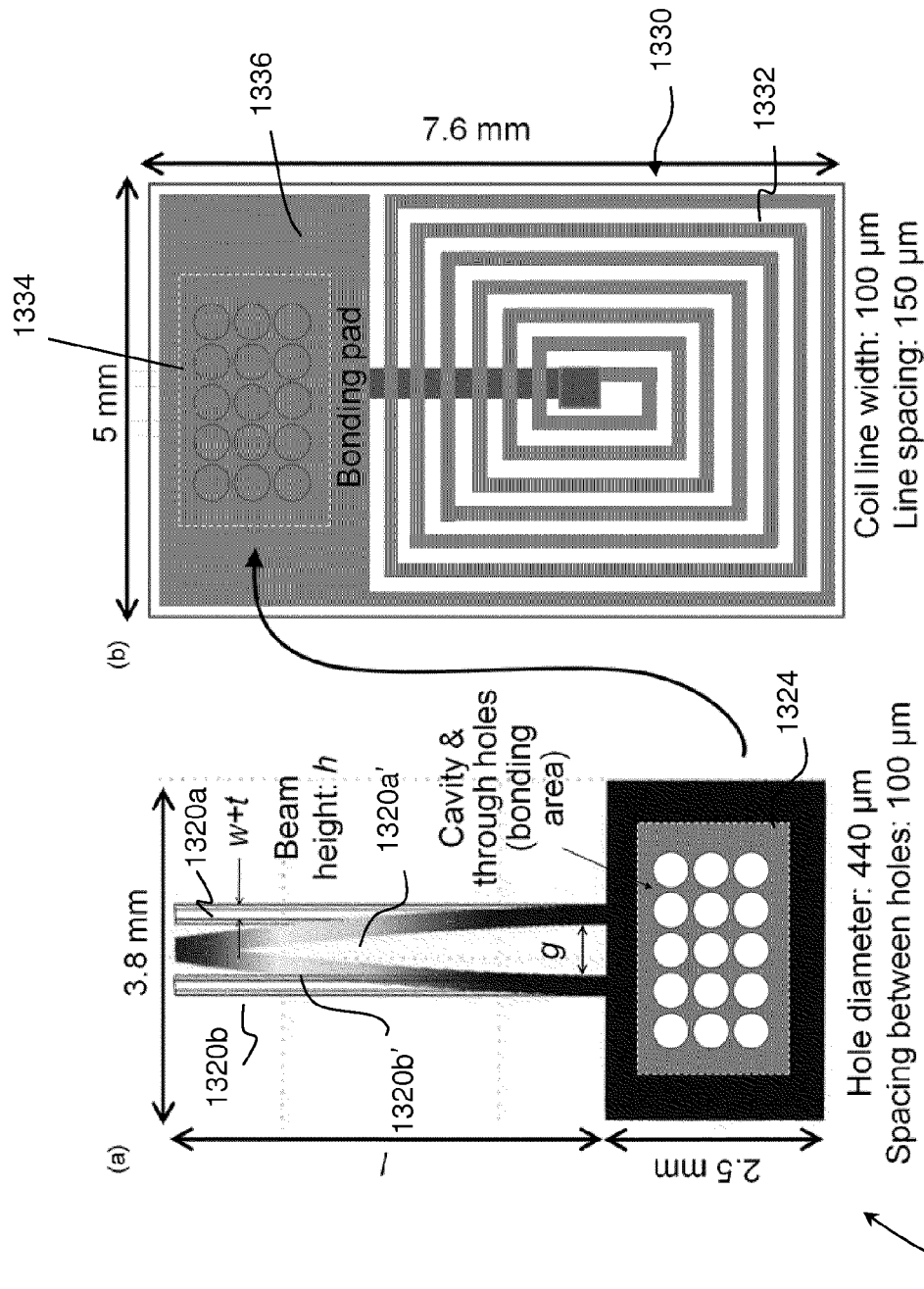
FIG. 14 shows (a) an illustrative SMA gripper design and (b) a sample layout of an LC circuit design.

FIG. 14 shows the layout of the SMA gripper structure 1322 and heater circuit 1330. In some embodiments, the grippers 1322 have a normally closed design with the cantilever member length of either 4 mm (e.g., as in device-1 below), 5 mm (e.g., as in device-2 below), or any other length between about 1 mm and about 10 mm. The gripper structures 1322 are formed by micro-electro-discharge machining (μEDM) of 300 μm thick Ti—Ni sheets with an austenitic-phase temperature of 65° C. (Alloy M, Memory Metalle GmbH, Germany). The outer sidewall of each of the two gripper beams 1320 is coated with a compressive SiO₂ layer. The dimensions of the gripper structures 1322 are summarized in Table 1 (below). The dimensions were determined using a finite element analysis tool (COMSOL Multiphysics 3.5a) to ensure that the beams 1320 close together in the cold state. (For example, the gap spacing of 570 μm between the beams 1320 for device-1 was determined by a computed displacement of 582 μm; the analysis utilized the data reported in B. A. Davis, "Investigation of the thermomechanical response of shape memory alloy hybrid composite beams," NASA/CR-2005-213929 for temperature-dependent material properties such as CTE and Young's modulus for Nitinol.)

The gripper 1322 also includes a bonding pad 1324 with a cavity and perforations as shown in FIG. 14. The bonding pad 1324 is bonded to either an optional copper bonding pad 1334 or a capacitor electrode 1336 on the heater circuit 1330, which includes a planar spiral coil 1332 with an overall size of 5×5 mm². The size, shape, and width and spacing of the lines that form the planar spiral coil 1332 may be selected depending on the desired resonant frequency, etc.

TABLE 1

Dimensions of the gripper structures.

| Dimensions | Device-1 | Device-2 |
|---|---|---|
| Beam length, l (mm) | 4 | 5 |
| Beam width, w (μm) | 62 | 70 |
| Beam height, h (μm) | 300 | 300 |
| SiO₂ thickness, t (μm) | 3 | 4.2 |
| Gap spacing between beams, g (μm) | 570 | 600 |

Figure 15:
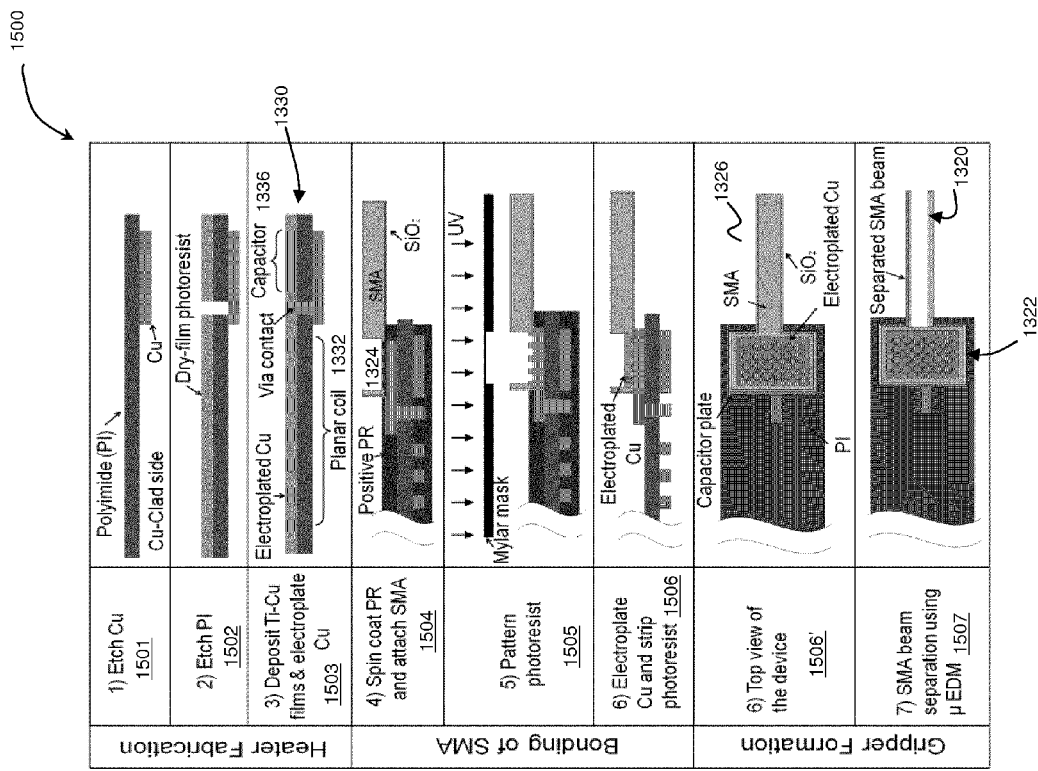
FIG. 15 illustrates a fabrication process flow for illustrative SMA devices.

FIG. 15 shows an illustrative fabrication process 1500 for a device 1300 with an SMA component (grippers 1322) bonded on the capacitive electrode 1336 of the heater circuit 1330. In some embodiments, the planar LC circuit 1330 is fabricated using single-sided copper-clad PI film with 50 μm thickness (G2300, Shehdahl Co., MN, USA). Photolithography for the circuit fabrication is performed with dry-film photoresists (15 μm thick MacDermid SF306 and 38 μm thick DuPont PM240). First, one of the capacitor electrodes 1336 is formed by wet etching of the copper-clad layer by using patterned SF306 photoresist as a mask (FIG. 15, step 1501). Next, the PI film is etched using a KOH-based solution to create a via contact hole in the film (FIG. 15, step 1502). After depositing a titanium-copper seed layer on the PI side, copper electroplating in the patterned PM240 photoresist mold is performed in a sulfuric-acid-based bath at a current density of 32.3 mA/cm² for 30 minutes to form the coil 1332 and the other capacitor electrode 1336 with a thickness of 30-35 μm (FIG. 15, step 1503).

Figure 16:
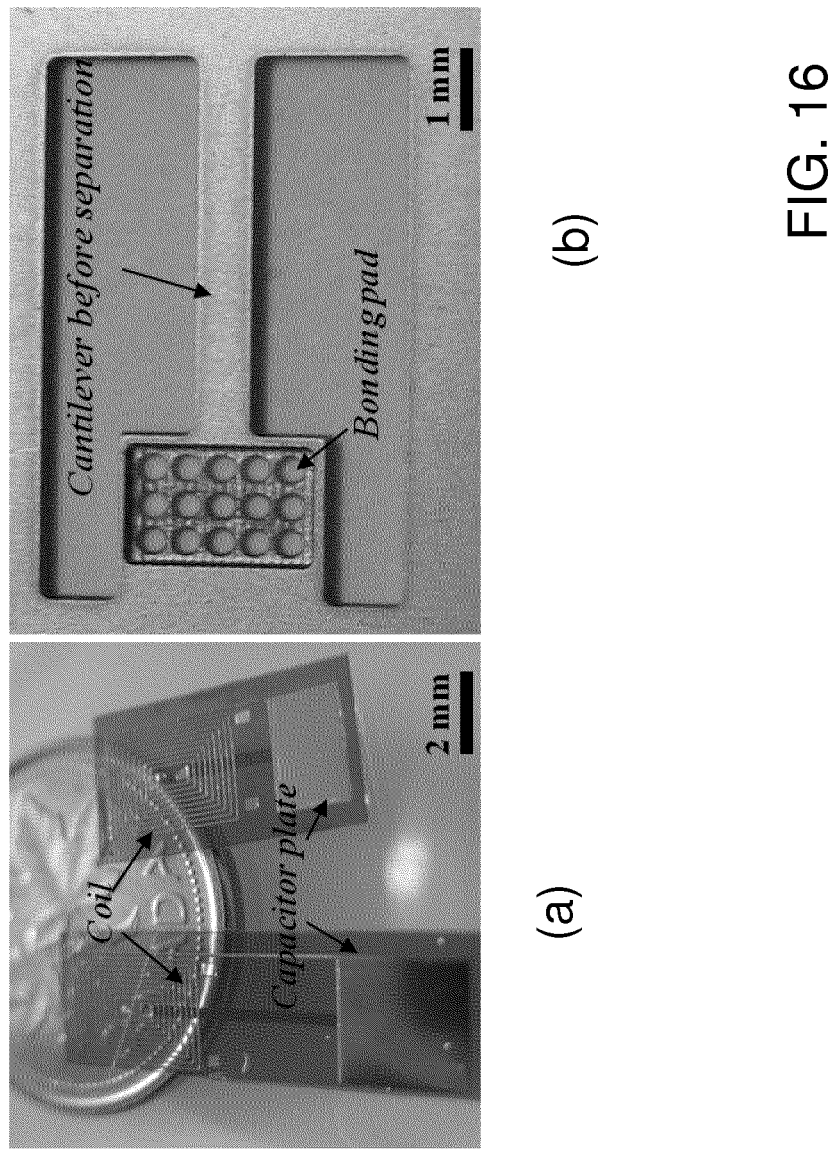
FIG. 16 shows (a) illustrative samples of the LC resonant circuit fabricated using copper-clad polyimide (PI) film, and (b) an illustrative SMA gripper component fabricated with μEDM (prior to separation from the original sheet).

At the same time, the SMA gripper 1322 is fabricated by shaping a piece of the SMA sheet using μEDM to form an SMA component 1326 with a single-beam structure (not shown). This is followed by the deposition of SiO₂ film, which serves as the reset layer, on each side of the SMA piece using plasma-enhanced chemical vapor deposition (PECVD) at 350° C. or any other suitable technique. The thickness of the SiO₂ in each deposition is set to be half of the final thickness of the layer listed in Table 1, so that the target thickness is achieved on the sidewalls of the beam upon the completion of the two-step depositions. The SMA component 1326 is then μEDMed to create the bonding pad 1324 with the cavity and perforations (e.g., as shown in FIG. 16(*b*)). This μEDM step removes the SiO₂ layer from the pad region.

The bonding pad 1324 of the SMA component 1326 is fixed onto the capacitive electrode 1336 on the copper-clad side of the circuit 1330 coated with photoresist (SPR 220-7, Rohm and Haas Co., PA, USA) that works as a temporary adhesive (FIG. 15, step 1504). The photoresist is then soft baked for ten minutes at 90° C., followed by lithography to remove the photoresist in the pad region (FIG. 15, step 1505). Then, copper is electroplated in the pad region under the condition described above to grow 120 μm thick bonding structures (FIG. 15, step 1506 (side view), 1506' (top view)); copper grown from the capacitor electrode 1336 through the pad's perforations is over-plated and connected to the portion plated on the pad 1324, mechanically fixing the pad 1324 to the capacitor electrode 1336. In this step, the SiO₂ layer on the SMA beam acts as a mask during electroplating so that copper is only deposited on the SMA cavity and the capacitor electrode through the perforations in the cavity. Once the bonding pad 1324 is secure, the SMA beam is separated to form the SMA cantilever members 1320 with vertical sidewalls (FIG. 15, step 1507).

FIG. 16(*a*) shows a pair of fabricated LC circuits 1322. Both the circuits in the figure were measured to have the same inductance of 292 nH but different capacitances of 15.6 pF (left circuit) and 9.4 pF (right circuit) due to their different electrode sizes, providing resonant frequencies of 75 MHz and 96 MHz, respectively. FIG. 16(*b*) shows a partially fabricated SMA component 1326. The SMA component 1326 has been μEDMed to create the bonding pad 1324 with the cavity and perforations, but has not been separated from the SMA sheet from which it is made. These split beams 1320 have inner sidewalls without $SiO_2$ layers, so they can bend and close their tips together due to the compressive $SiO_2$ layer present on the outer sidewalls. $SiO_2$ has compressive stress so when the SMA beams (1320) are not heated, the beams bend inward, causing the gripper to close. When the SMA beams are heated, the beams go back to the memorized straight shape (this force is larger than the compressive force exerted by the $SiO_2$'s) causing the gripper to open.

Figure 17:
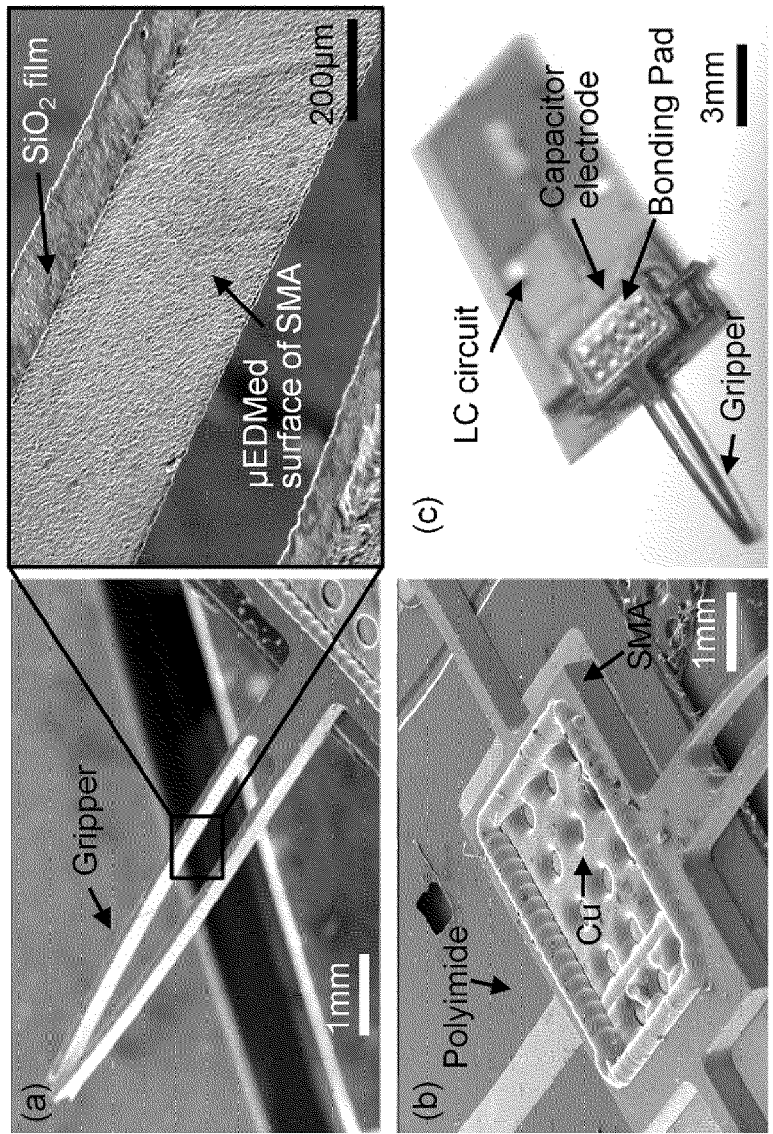
FIG. 17 shows fabrication results for an illustrative device-1 (4 mm long gripper), including (a) gripper beams split using μEDM with a close-up showing the inner sidewall of the beam; (b) the SMA pad bonded by electroplated copper; (c) the overall shape of a fabricated device.

FIGS. 17(*a*)-17(*c*) are photos of a microgripper device fabricated using the process 1500 of FIG. 15. FIG. 17(*a*) shows actuated cantilever members 1320—the tips are touching—and the inset to the left of FIG. 17(*a*) shows the μEDMed surface of one cantilever member's vertical wall. An $SiO_2$ film coats the upper surface of each cantilever member 1320. FIG. 17(*b*) shows the pad 1324 of an SMA gripper component 1322 bonded to the LC circuit 1330 by the electroplating process described with respect to FIG. 15. Copper coats part of the upper surface of the SMA, with polyimide on the heater circuit substrate. FIG. 17(*c*) shows the final device is shown in an actuated state.

Exemplification of SMA Microgripper Devices

Characterization results for the SMA material and fabricated microgripper devices are presented in this section. The performance of the devices is evaluated through wireless actuation tests as well as the manipulation of CNT samples. The electroplated bonding strength is measured with micromachined samples.

SMA Phase Transition Characteristics

Figure 18:
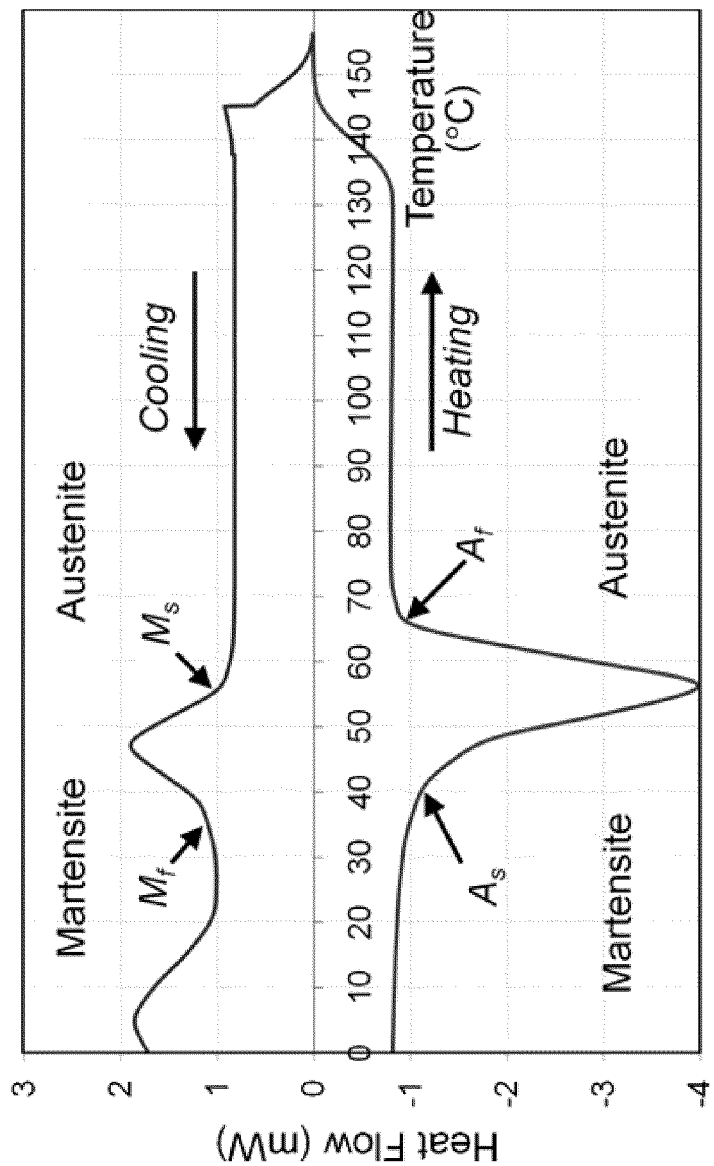
FIG. 18 shows measured heat flow versus temperature for the illustrative SMA material used for the device fabrication of FIG. 17.

In order to predict behaviors of fabricated devices, the SMA material used for the fabrication example given above was characterized using a differential scanning calorimeter (DSC Q1000, V9.0, build 275, Universal 4.1 D, TA Instruments, DE, USA) that measures the phase transformation temperatures by detecting changes in heat flow through the material. The sample was encapsulated in an aluminum pan and scanned at 20° C./min in both heating and cooling modes to determine the temperatures of austenitic start ($A_s$), austenitic finish ($A_f$), martensitic start ($M_s$), and martensitic finish ($M_f$). A typical measurement result is shown in FIG. 18. It can be seen in the result that $A_s$, $A_f$, $M_s$, and $M_f$ for the SMA are approximately 40° C., 65° C., 55° C., and 35° C., respectively. This indicates a transformation temperature hysteresis of about 5-10° C. for the material.

Wireless Actuation Tests

Figure 19:
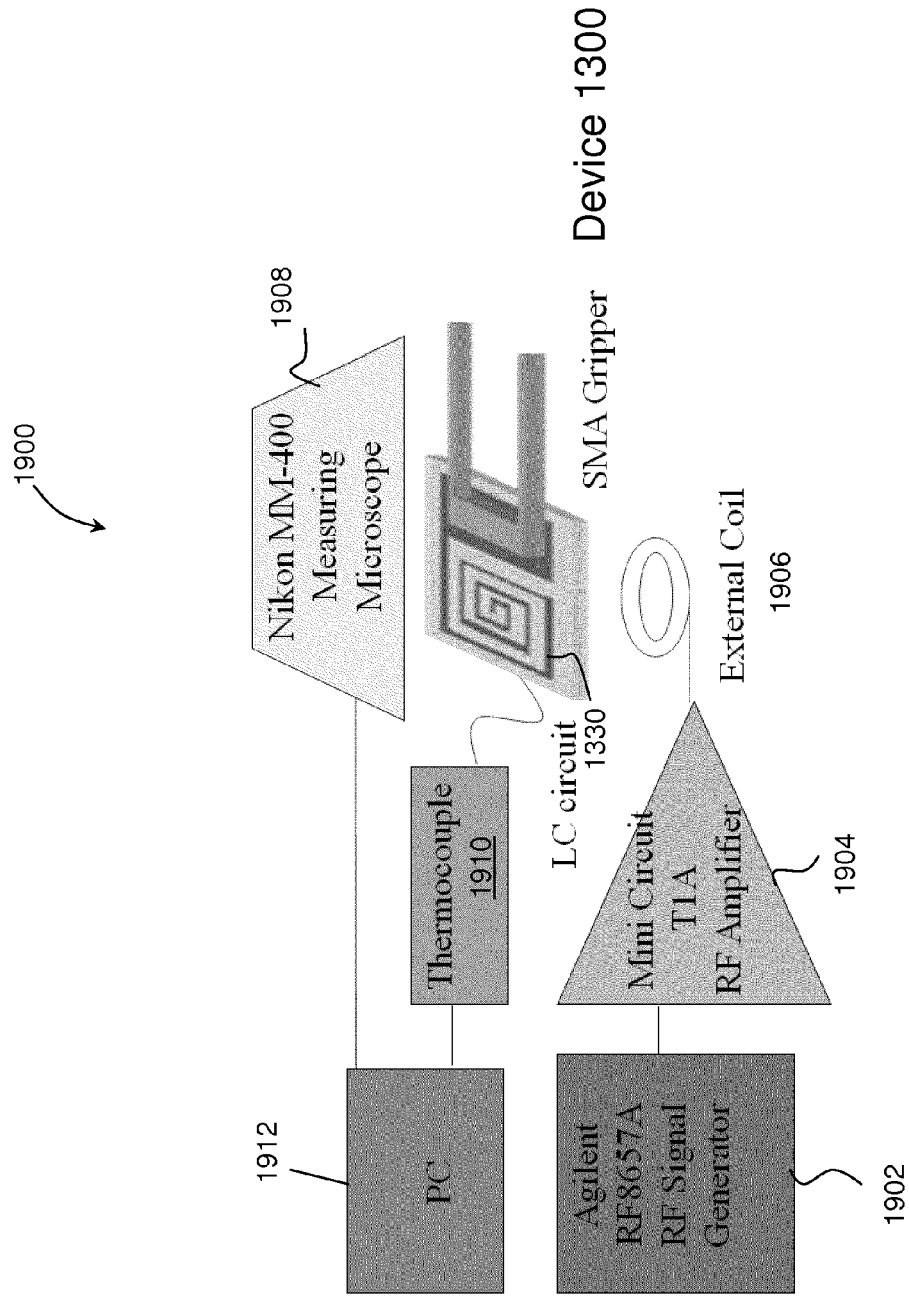
FIG. 19 shows a set-up for wireless actuation tests of illustrative SMA devices.

FIG. 19 illustrates a set-up 1900 used to test several microgripper devices 1300. In this set-up 1900, an rf signal generator 1902 generates an rf signal at or near the resonance frequency of the device under test. An rf amplifier 1904 coupled to the rf signal generator 1902 amplifies to signal to a power of up to 1 W. The amplified rf signal drives an external coil 1906 (diameter about 4 mm, 497-nH inductance) to generate an RF magnetic field that excites the LC circuit 1330 of the gripper device 1300. The thermo-mechanical behavior of the gripper device 1300 was characterized using a thermocouple 1910 attached to the gripper device 1300 (on the capacitor electrode not bonded with the SMA) as well as a measuring microscope 1908 with a resolution of 0.1 μm to characterize the displacement of the gripper. A PC 1912 coupled to the microscope 1908 and thermocouple 1910 captured and processed data. (It was verified experimentally that the dependence of thermocouple reading on the presence of magnetic fields at the power levels and frequencies used in the tests was minimal or undetectable.)

Figure 20:
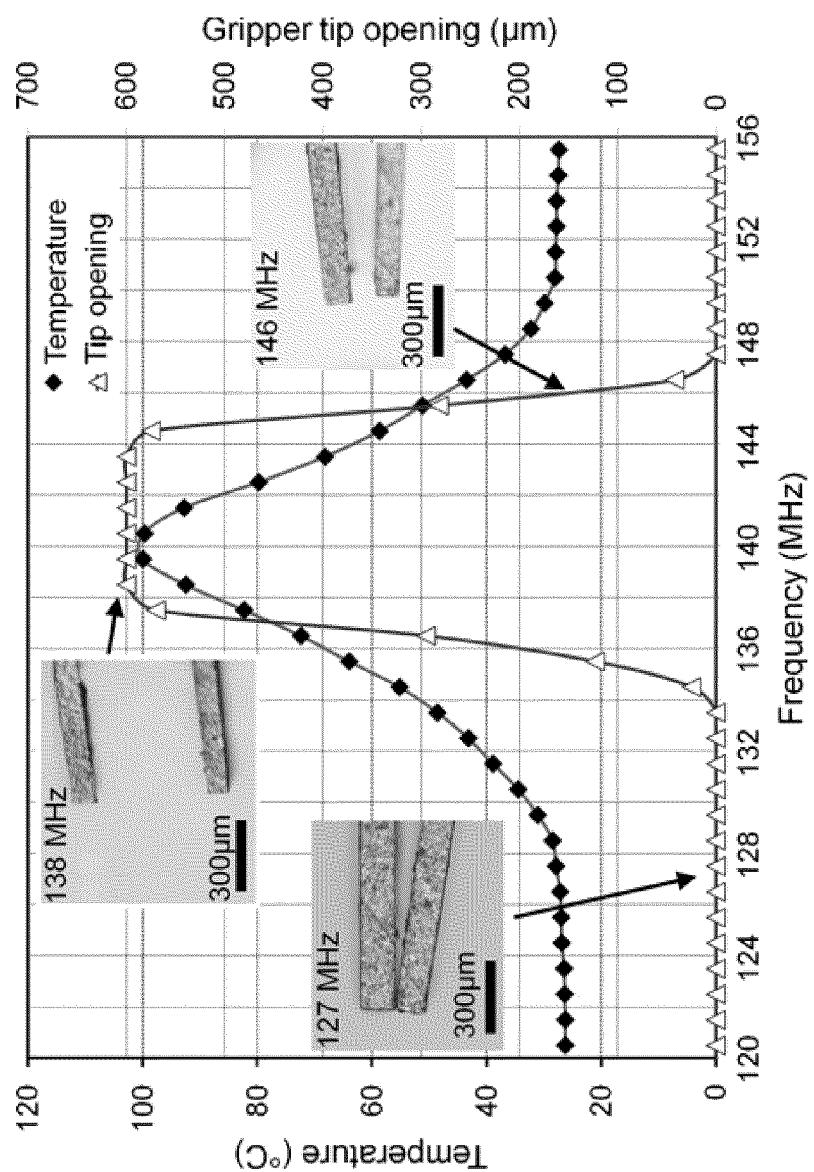
FIG. 20 shows measured circuit temperature and gripper opening versus field frequency (inset images show tip openings of the gripper at corresponding frequencies).

FIG. 20 is a plot of device temperature (left axis) and gripper tip opening (right axis) versus field frequency for a microgripper device-2 with 5 mm long cantilever members 1320. The resonant frequency of the device's LC circuit 1330 was measured to be about 140 MHz (with L=184 nH and C=7 pF). The circuit temperature and gripper displacement (tip opening) were measured simultaneously using the apparatus shown in FIG. 19 while scanning the field frequency from 120 MHz to 155 MHz at a constant output power of 0.2 W. The measurement results show a strong temperature peak (of 100° C.) when the field frequency was aligned to the resonant frequency. The results also indicate that the gripper 1322 was activated and deactivated at about 48° C. and 37° C., respectively, indicating an active frequency range (the difference between the field frequencies at these two points) of 13 MHz. The gripper was open to its maximum opening, 600 μm, when the device temperature was reached and started to drop at about 92° C. and 68° C., respectively.

The four measured temperatures, which in order correspond to $A_s$, $M_f$, $A_f$, and $M_s$, tended to be higher than the measured phase transition temperatures of the material used. This may be because the temperature was probed on the circuit 1330 at a distance from the SMA gripper 1322; the actual temperatures of the SMA gripper 1322 are possibly lower than the measured values in FIG. 20 due to heat loss between the probing location and the SMA. The temperature values from FIGS. 18 and 20 suggest that a temperature difference between the heater circuit and the gripper is around 27° C. (the difference between the measured $A_f$ in FIG. 18 and the corresponding temperature in FIG. 20 noted above) or less.

Figure 21:
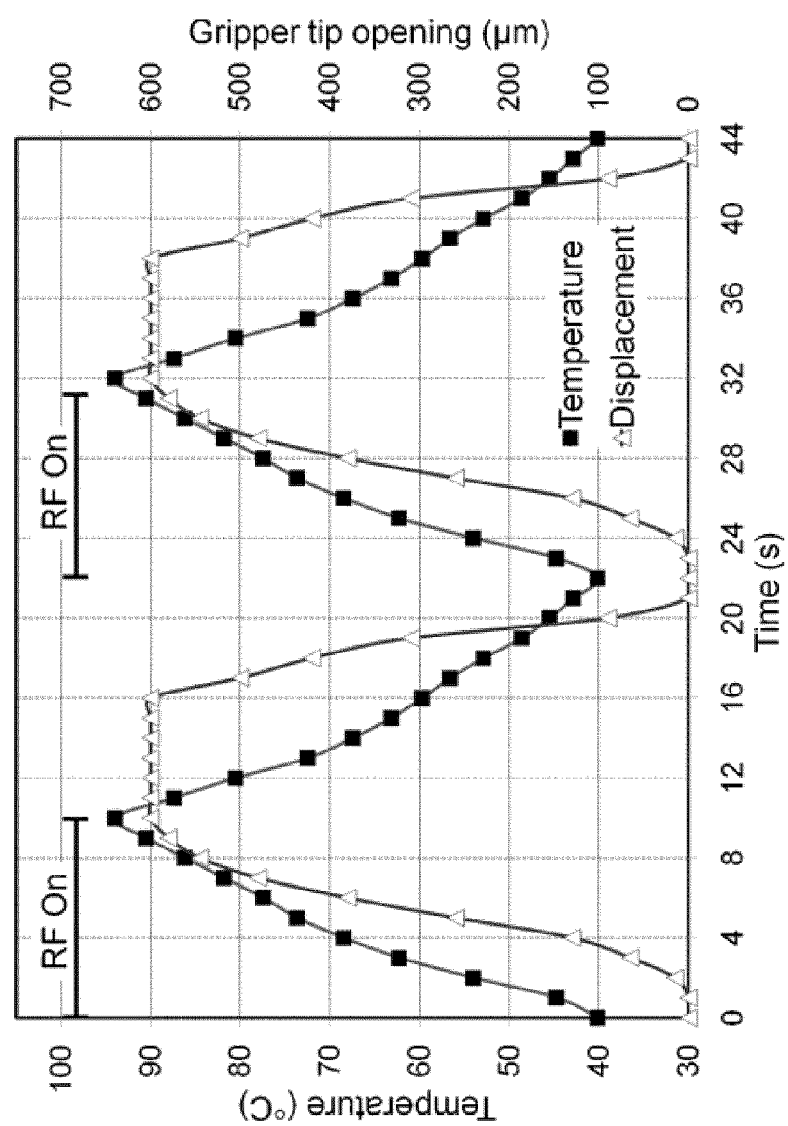
FIG. 21 shows measured circuit temperature and gripper opening resulting from repeated excitations with an external RF magnetic field whose frequency was aligned to the resonant frequency of an illustrative circuit.

FIG. 21 is a plot of device temperature (left axis) and gripper tip opening (right axis) versus time for a gripper device subject to an external magnetic field that pulsed on and off. When on, the field had a 0.2W output power at resonance (140 MHz). FIG. 21 shows that the gripper opened its maximum opening of 600 μm (at 94° C.) from its fully closed state (at 40° C.) about nine seconds after the field was turned on, whereas the gripper took about five seconds to return to its fully closed state after the field was turned off. These suggest that this gripper may be operated for the full-range actuation in a 14-second cycle (about 0.07 Hz) with the set-up 1900 used in FIG. 19. The time response of the actuation depends on the RF output power used for the device excitation as well as the device design/size including the SMA material (i.e., its austenitic-phase temperature) used.

Figure 22:
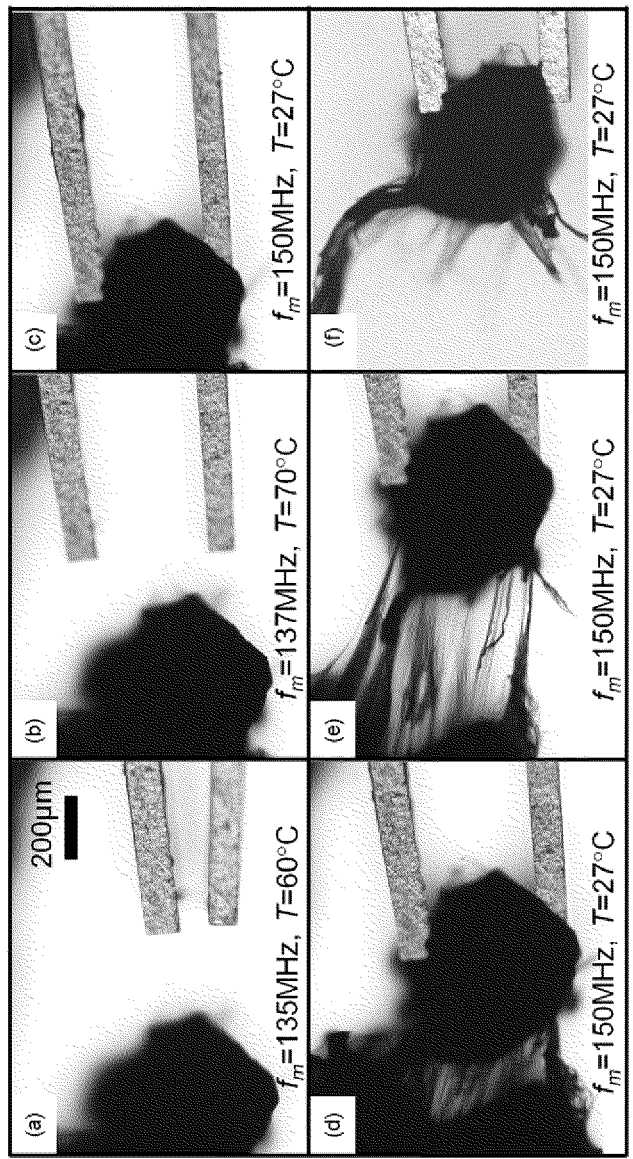
FIG. 22 illustrates different stages of manipulation of a carbon nanotube (CNT) forest ($f_m$ and T in each image are the field frequency and the circuit temperature, respectively) with an illustrative gripper device: (a) approaching the forest; (b) opening the tips of the gripper device by tuning $f_m$ closer to the device's resonant frequency of 140 MHz; (c) making contact with the forest, and closing the tips by shifting $f_m$ to 150 MHz; (d) pulling the gripped part of the forest; (e) continuing to pull the forest part; (f) showing the separated forest part held by the gripper.

FIGS. 22(*a*)-22(*f*) are photographs of an rf-controlled gripper device grabbing and pulling a carbon nanotube (CNT) forest. For this test, a gripper device with 140-MHz resonant frequency was attached to a micro positioner (Manipulator 750, Signatone Co., CA, USA) that was used to manually position the gripper device relative to a CNT forest sample. FIG. 22(*a*) shows the gripper approaching the forest sample at a device temperature of about 60° C. with a field frequency of 135 MHz. In FIG. 22(*b*), the device temperature is increased to about 70° C. by tuning the field frequency closer to the resonant frequency of the device, and the gripper continues to approach the sample. In FIG. 22(c), the gripper makes contact with the CNT forest, and the tips are closed to grab a part of the forest by shifting the field frequency to 150 MHz, bringing the device temperature down to 27° C. From FIG. 22(d) to FIG. 22(e), the gripper is moved apart from the forest sample, and continues to be pulled until the part of the forest it is gripping separates from the rest of the forest. FIG. 22(f) shows the gripper holding the separated part of the forest.

Characterization of Bonding Strength

Figure 23:
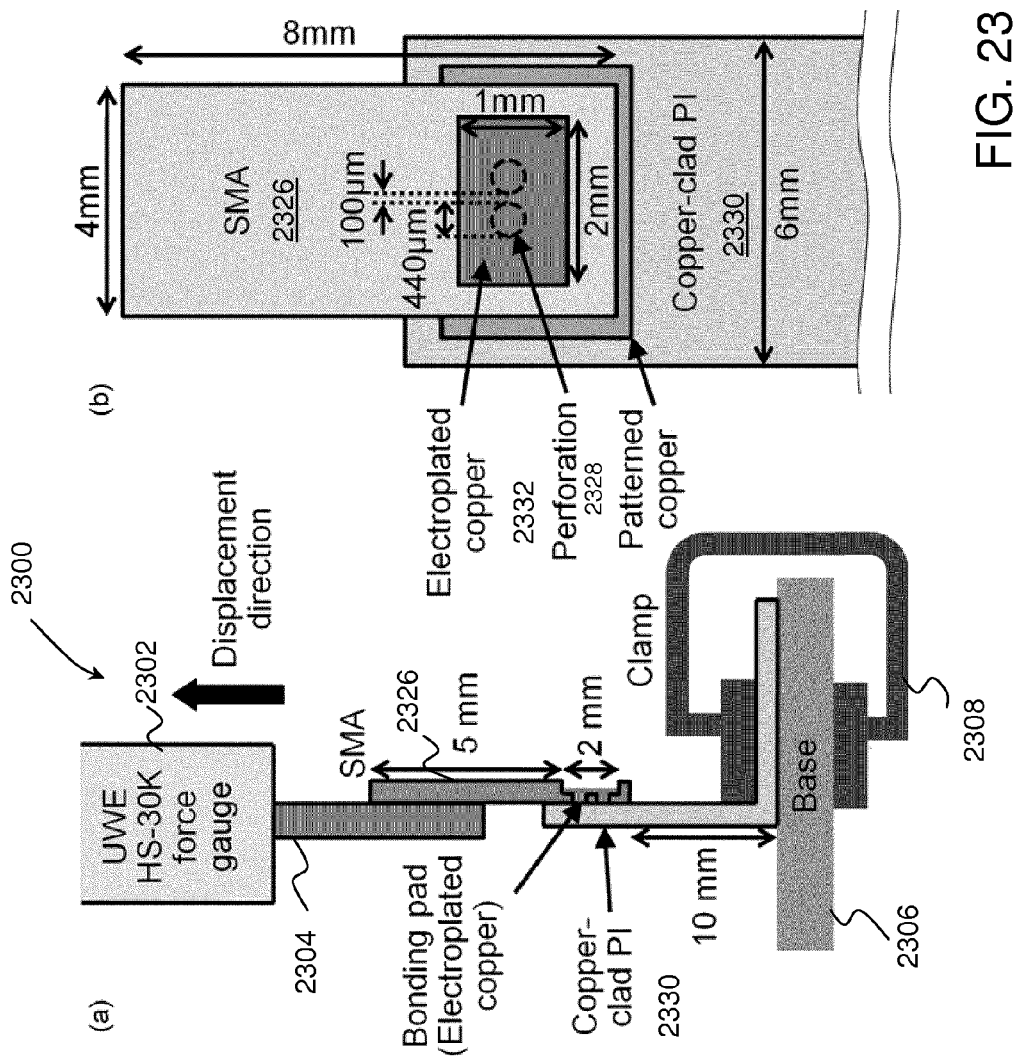
FIG. 23 shows (a) a cross-sectional view of an illustrative set-up for measuring shear bonding strength and (b) the layout of illustrative SMA samples used for the shear bonding strength measurement.

FIG. 23(a) is a cross-sectional view of a peeling-test apparatus 2300 used to characterize the bonding strength provided by the developed electroplating process described above in light of its potential application to the fabrication of MEMS and micro-mechanical devices. The peeling tests performed with the apparatus 2300 measured the shear strength of an electroplated copper microstructure formed by bonding SMA components 2326 to copper-clad PI substrates 2330. The strength was characterized using a force gauge 2302 (UWE HS-30K, Intelligent Weighing Technology Inc., CA, USA) attached to the sample under test.

FIG. 23(b) shows the layout of the samples used for the peeling test; each SMA component 2326 was machined from a 300 μm sheet to have two 440 μm diameter perforations 2328 with 100 μm spacing in a 280 μm deep 1×2 mm$^2$ cavity. Each SMA component 2326 was bonded to a copper-clad PI substrate 2330 through the two perforations 2328 by electroplating a 120 μm thick layer of copper onto a region 2332 around the perforations 2328 using the process described above. To test each sample, as illustrated in FIG. 23(a), a portion of the PI substrate 2330 was coupled to a base 2306 with a clamp 2308 and bent by 90° so that the SMA component 2326 pointed upward. The SMA component 2326 was fixed to the force gauge 2302. Shear forces were then applied to the sample by displacing the gauge 2302 vertically using a micrometer (not shown) while measuring the forces with the gauge until the bonding failed.

Figure 24:
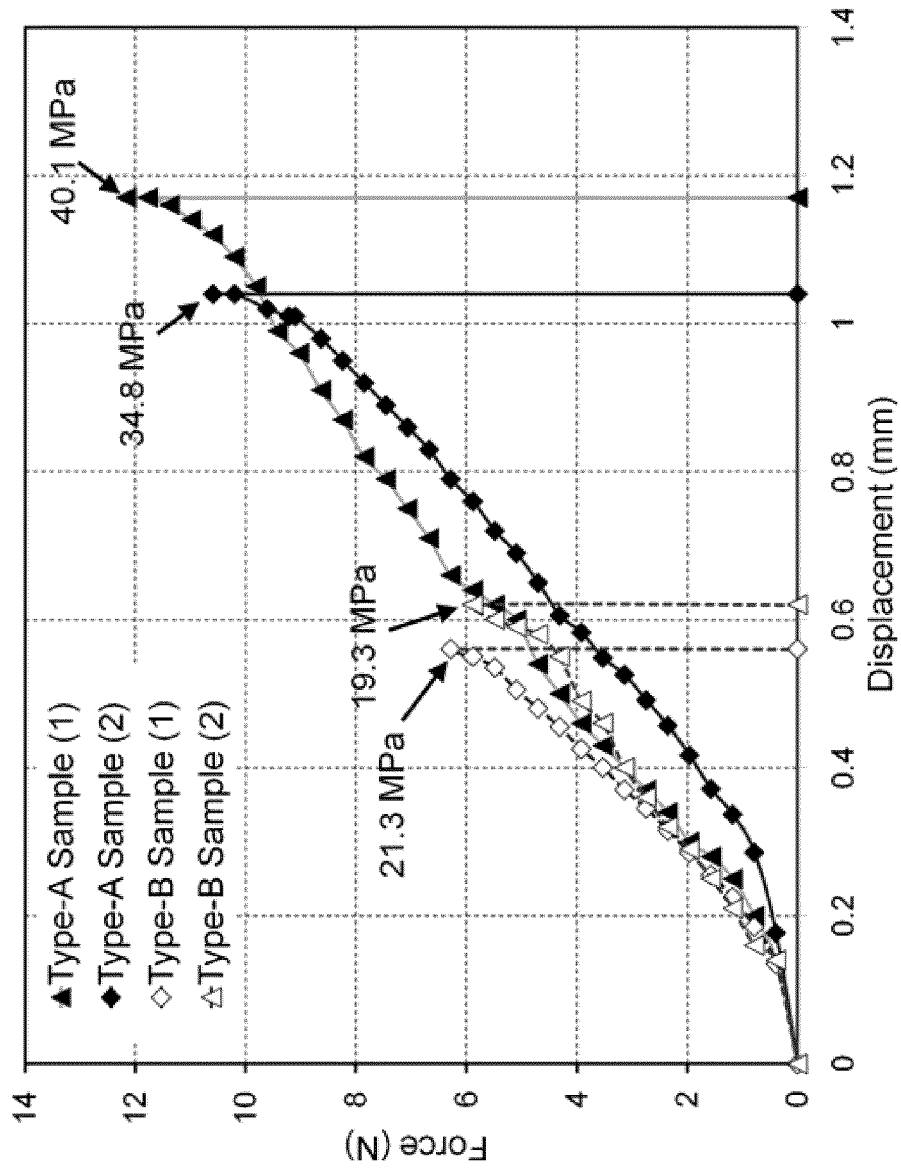
FIG. 24 shows measured shear forces versus displacement for illustrative type-A (with $SiO_2$ layer) and illustrative type-B (without the layer) samples, showing the shear strengths calculated using the bonding surface area of 0.304 $mm^2$.

In order to evaluate the effect on the bonding strength of the SiO$_2$ insulation layer coated onto SMA, samples with (type-A) and without (type-B) SiO$_2$ layers were prepared for the measurement. The type-A samples were fabricated in the same manner as the SMA gripper components described above, i.e., all the surfaces of each sample were first coated with SiO$_2$ and then the cavity was machined to form the bonding pad (thus no SiO$_2$ on the bonding-pad surfaces). The results of the shear tests on type-A and type-B (using two samples each) are plotted in FIG. 24, which shows that the type-A samples with SiO$_2$ layer had much higher shear strengths than the type-B samples. The type-A samples broke when subjected to a force of 10.6-12.2 N, corresponding to shear strengths of 34.8-40.1 MPa (over 0.304 mm$^2$, the total area of the two perforations). The type-B samples were observed to exhibit shear strengths of only 19.3-21.3 MPa. This large difference in bonding strength between the two types was attributed to differences in the electroplated copper structures in the SMA perforations.

Figure 25:
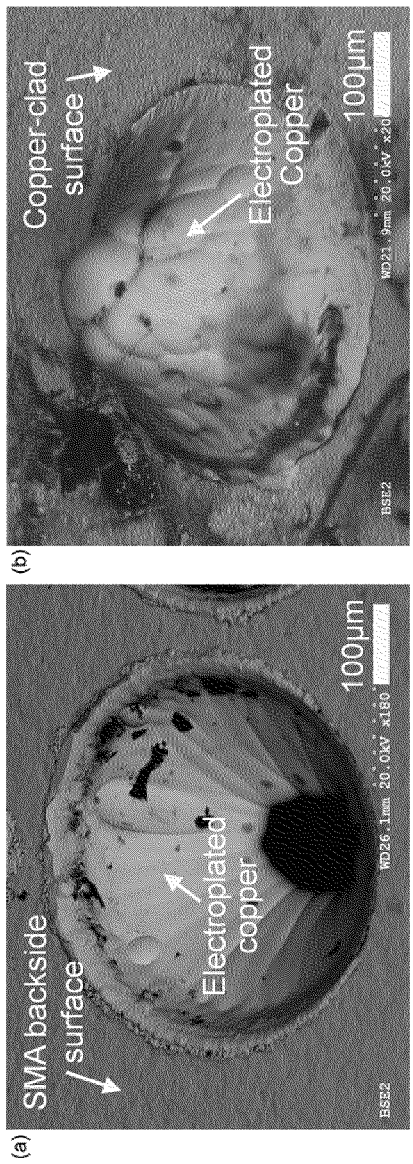
FIG. 25 shows scanning electron microscope (SEM) images of a broken interface in an illustrative type-B sample, including (a) the backside of the SMA showing the bowl-like electroplated copper structure grown from the edges of the perforation narrowing the opening; and (b) the electroplated copper bump structure formed on the copper-clad layer underneath the bowl-like structure in (a).
Figure 26:
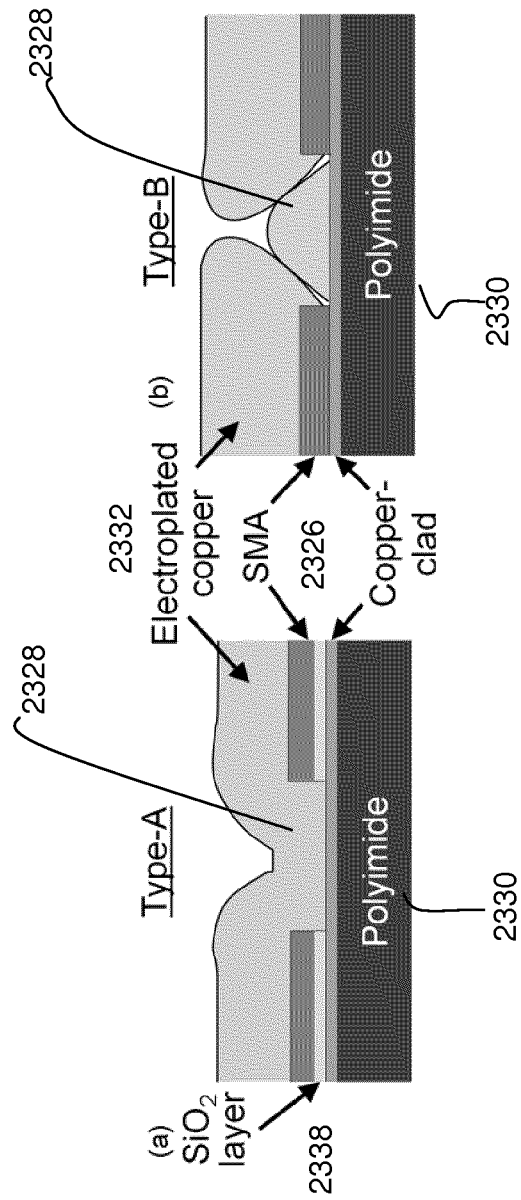
FIG. 26 is a cross-sectional diagram of copper structures in (a) an illustrative type-A sample (with $SiO_2$ layer) and (b) an illustrative type-B sample (without the layer) formed by the electroplating bonding process.

FIGS. 25(a) and 25(b) are photographs of the broken interface structures of electroplated copper seen on the backside of the SMA perforation and on the top surface of the copper-clad PI substrate, respectively. FIG. 25(a) shows that the copper structure formed on the perforation has a bowl-like shape with the top opening narrowed by the grown copper structure, whereas FIG. 25(b) indicates a cone-shaped bump electroplated on the copper-clad surface. It appears that because type-B samples are electrically short circuited to the substrate (as there is no SiO$_2$ layer present on the SMA), copper grows quickly on the SMA, closing the top opening of the perforation 2328 and preventing further plating on the copper-clad surface as shown in FIG. 26(b). In contrast, the SMA component 2326 of type-A samples is initially isolated from the substrate 2330 due to the presence of an SiO$_2$ layer 2338, prohibiting copper growth on top of the SMA component 2326 and around the perforations 2328. As the copper structures in the perforations 2328 grow, they short circuit the SMA component 2326 to the substrate 2330; then copper starts to grow on the SMA component 2326 as well. With further plating, the copper layer 2332 grown on the SMA component 2326 connects with the over-plated structures grown through the perforations 2328, forming a solid, continuous bonding structure as shown in FIG. 26(a).

Figure 27:
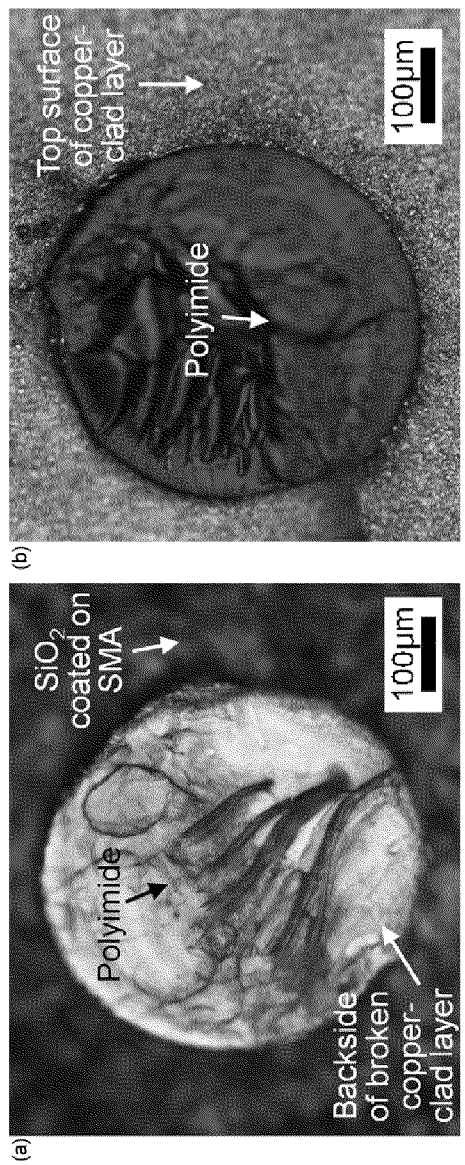
FIG. 27 shows illustrative optical images of the broken interface in a type-A sample, including: (a) an $SiO_2$ surface on the SMA showing that the portion of copper-clad layer bonded to the SMA through the copper structure electroplated in the perforation came off (together with some parts of PI) with the SMA when bonding failed; and (b) the copper-clad layer where the failure occurred showing the PI surface exposed.

FIG. 27 are photographs of the broken interface in a type-A sample. FIG. 27(a) shows an SiO$_2$ surface on the SMA component; the portion of copper-clad layer bonded to the SMA through the copper structure electroplated in the perforation came off (together with some parts of PI) with the SMA component when bonding failed. FIG. 27(b) shows the copper-clad layer where the failure occurred showing the PI surface exposed. The broken interfaces of the type-A samples indicate that the mechanical failure occurred at the interface between the copper-clad layer and the PI substrate, not at the bonding interface. This means that the actual bonding strength is greater than the measured shear strength values (34.8-40.1 MPa) and that the bonding method provides adhesion strengths that are considerably greater than the 8-30 MPa adhesion strengths available with conventional polymer-adhesive techniques.

Part III: SMA Microactuators for Microfluidics

Additional SMA devices of the present technology can be used for microfluidic control using external radiofrequency magnetic fields. For example, selective microfluidic control can be implemented with an array of illustrative SMA devices, each of which is thermally coupled to a wireless resonant heater which generates heat only when the field frequency is tuned to the resonant frequency of the heater as described above. Multiple actuators coupled to respective heater circuits, each of which has a different resonant frequency (e.g., in the range of 1-1000 MHz, 10-500 MHz, 50-400 MHz, or 135-295 MHz), can be selectively and simultaneously controlled by modulating the field frequency to the resonant frequencies of the corresponding heaters. When the temperature of the actuator exceeds the austenite-phase temperature of the SMA, the SMA is actuated as the material returns to its remembered shape. The frequency-modulation pattern and excitation interval time can be adjusted so that the achieved temperatures of the excited SMA structures exceed the threshold temperature using a fixed output field power high enough to reach the temperature. The shape of the actuator is restored to its original cold-state shape when heat is removed due to the force provided by the reset layer deposited on the SMA.

One example of the present technology includes a wireless microsyringe device that has three actuator-heater components and a flexible parylene reservoir. The microsyringe has a reservoir that contains up to 5, 10, 15, 20, or 25 μL of fluid (e.g., pharmaceutical compound) and one or more cantilever-type actuators to eject a controlled amount of liquid from the reservoir. Each cantilever-type actuator may be 1, 2.5, 5, 10, or 15 mm long. In one example, the reservoir is loaded with an acidic solution and used to perform sequential modifications of the pH level in a liquid through the selective release of the acidic solution by three actuators. The thermal characterization of each actuator using infrared imaging shows a temperature increase of 50° C. in 4 seconds and the full activation of the actuator in eight seconds with 300-mW field output power.

Figure 28:
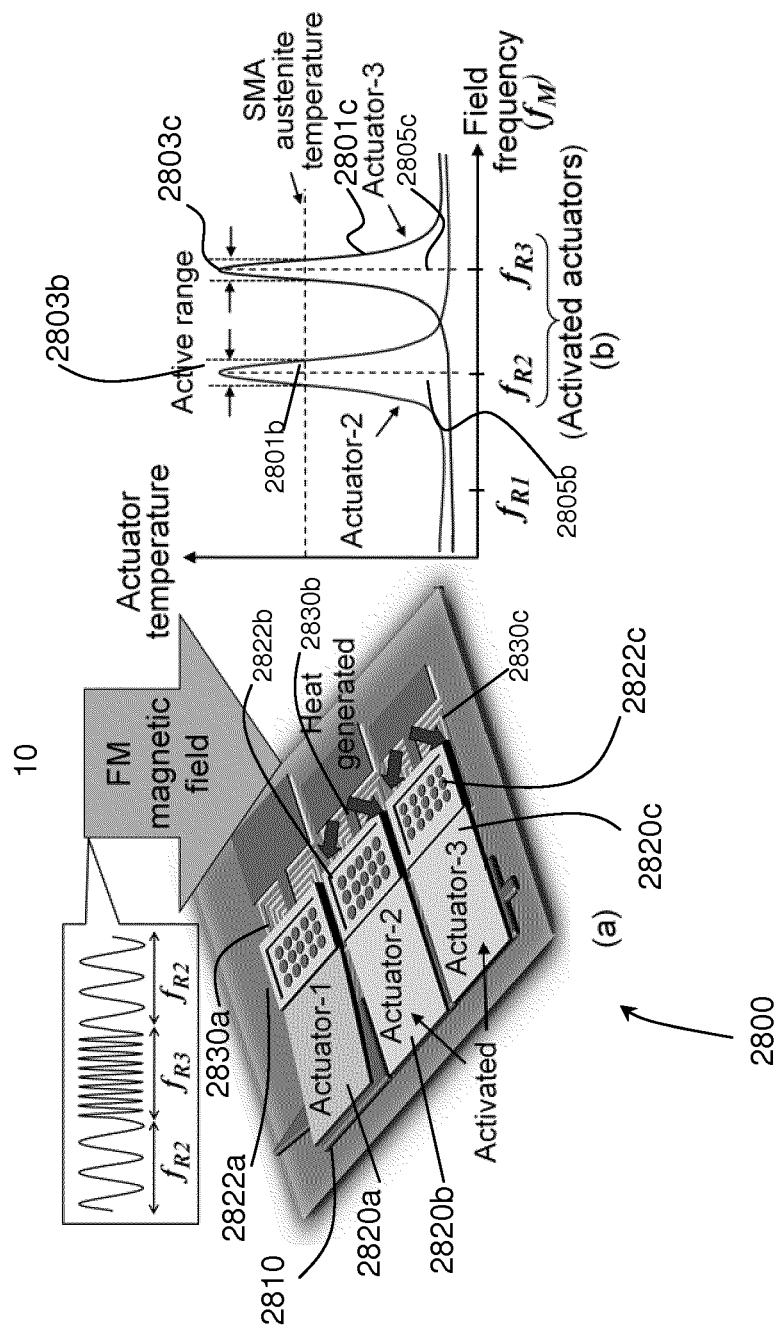
FIG. 28 illustrates (a) an illustrative microsyringe/injector with multiple, selectively controlled SMA actuators thermally coupled to respective resonant heater circuits and (b) a plot showing device temperature versus resonant frequency when the device is subject to a magnetic field whose frequency ($f_M$) is modulated to match the resonances of two of the resonant heater circuits ($f_{R2}$ and $f_{R3}$).
Figure 29:
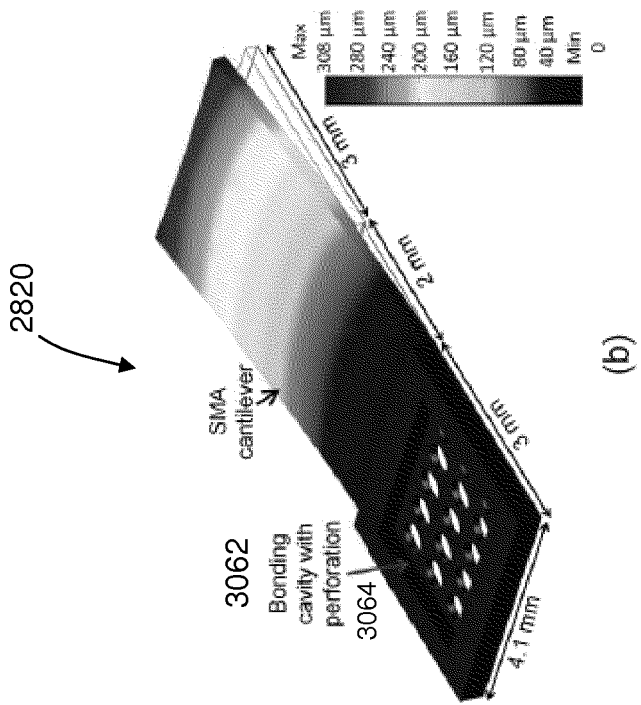
FIG. 29 shows (a) an illustrative microsyringe/injector design and (b) a finite element analysis model of the SMA actuator of FIG. 28(a) showing an approximate displacement of 300 μm at the free end due to the force provided by a 3.5 μm thick $SiO_2$ layer on the backside of the SMA, indicating the space created underneath the actuator is large enough to accommodate a 130 μm thick parylene reservoir.
Figure 29:
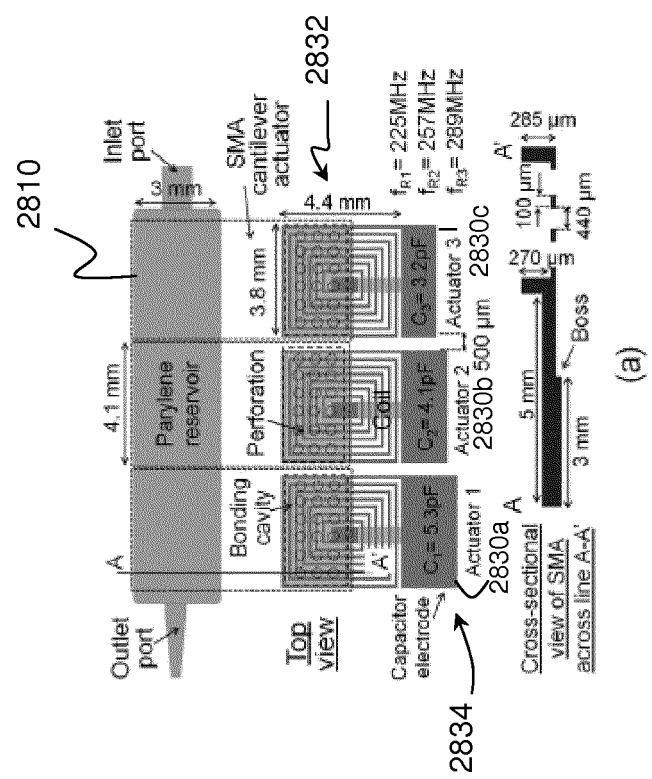

FIGS. 28 and 29 illustrate aspects of an illustrative microsyringe device 2800 based on thermal activation of SMA actuators 2830a, 2830b, and 2830c (collectively, SMA actuators 2830). The device 2800 includes a flexible reservoir 2810 that is filled with a liquid or gel and squeezed by three cantilever-type SMA actuators 2830 with identical dimensions (e.g., 5 mm length and 4.1 mm width) arranged in an array to eject the liquid or gel from the reservoir 2810. The ejection amount is controlled by the number of actuators 2830 activated. Each SMA cantilever 2820 is micromachined to have a bonding cavity 2822 with perforations, which are used to permanently bond the SMA cantilever 2820 onto a respective heater circuit 2830 using the electroplating bonding technique described above. The bonding also places each SMA cantilever 2820 in thermal communication with a respective heater circuit 2830. The reservoir 2810, which may have a thickness of 130 µm, can be created on the backside of the heater circuits 2830 as shown in FIG. 29(a), such that an array of the SMA actuators is arranged above the reservoir 2810 when the SMA actuators 2820 are bonded to the heater circuits 2830.

Each heater circuit 2830 absorbs electromagnetic energy, or resonates, at a different frequency. Applying a frequency-modulated (FM) magnetic field 10 modulated at a given heater circuit's resonant frequency causes the given heater circuit 2830 to absorb electromagnetic energy, which, in turn, causes the heater circuit 2830 to heat up. Heat flows from the given heater circuit 2830 through the electroplated bonding region to a respective SMA cantilever 2820, which bends when heated above its austenitic-phase temperature. As the respective SMA cantilever 2820 bends, it compresses at least a portion of the reservoir 2810 so as to eject fluid from the reservoir 2810.

FIG. 28(b) is a plot of actuator temperature versus magnetic field frequency for the device 2800 shown in FIG. 28(a). Each heater circuit 2830 has a resonance 2801 that can be defined by a respective center frequency 2805, or resonant frequency $f_R$, and a respective active width 2803. (FIG. 28(b) shows only resonances 2801b and 2801c, center frequencies 2805b ($f_{R2}$) and 2805c ($f_{R3}$), and active widths 2803b and 2803c for heater circuits 2830b and 2830c, respectively.) In the case illustrated in FIGS. 28(a) and 28(b), the incident magnetic field 10 includes spectral components at $f_{R2}$ and $f_{R3}$ that are absorbed by heater circuits 2830b and 2830c, respectively, to heat actuators 2820b and 2820c above their SMA austenite temperatures. The increase in temperature causes actuators 2820b and 2820c to flatten out, as shown in FIG. 28(a). Actuator 2820a remains in its relaxed (bent) state because heater circuit 2830a does not resonate at $f_{R2}$ or $f_{R3}$.

Each active width 2803 may be 100 kHz, 250 kHz, 500 kHz, 1 MHz, 2 MHz, 5 MHz, 10 MHz, or any other suitable bandwidth. Different heater circuits 2830 may have different active widths or the same active width. Similarly, each center frequency 2803 may be between about 10 MHz and about 200 MHz, between about 50 MHz and about 150 MHz, between about 80 MHz and about 140 MHz, e.g., 100 MHz, 110, MHz, 120 MHz, or any other suitable value. The center frequencies 2805 of the different heater circuits may be separated from each other by different amounts or the same amounts, e.g., 1 MHz, 2.5 MHz, 5 MHz, 10 MHz, 12.5 MHz, 15 MHz, 20 MHz, or any other suitable value.

As will be appreciated by those of skill in the art, the magnetic field 10 may be modulated at a single resonant frequency, at multiple resonant frequencies, or at alternating combinations of single and multiple resonant frequencies as desired. For instance, the magnetic field 10 may be modulated such that the actuators 2820 squeeze the reservoir in a predetermined order, e.g., actuator 2820a, then actuator 2820b, and finally actuator 2820c. Alternatively, the magnetic field 10 may be modulated such that the actuators 2820 expel a predetermined amount of fluid, where each actuator 2820 is configured to expel a different amount of fluid from the reservoir 2810. For instance, actuator 2820a may expel 1 µL, actuator 2820b may expel 2 µL, and actuator 2820c may expel 3 µL, and the actuators 2820 may be activated in combination or alone. Alternatively, each actuator 2820 may be configured to expel the same amount of fluid from the reservoir 2810. The device 2800 may also include more or fewer actuators 2820 and resonant heater circuits 2830. Alternative devices 2800 may also include multiple actuators 2820 thermally coupled to a single heater circuit 2830.

In one example, the SMA structures 2820 are bulk micromachined in 300 µm thick Ni—Ti sheets with an austenitic-phase temperature of 65° C. (Alloy M, Memory Metalle GmbH, Germany). The bottom side of each SMA structure 2820 is coated with a compressive reset layer at a temperature greater than 65° C., i.e., the layer is deposited on flat cantilevers 2820 in a trained state. After the deposition, at room temperature (<65° C.), the coated SMA cantilever 2820 bends due to the compressive stress applied by the reset layer. The coated SMA cantilever 2820 returns to its trained flat shape when heated to a temperature greater than 65° C.

FIG. 29(b) shows a finite element analysis of a deformed actuator 2820 performed using a finite element analysis tool (COMSOL Multiphysics™ 3.5a). The finite element analysis helps to ensure that the cold-state bent SMA cantilever 2820 forms a space large enough to accommodate the reservoir 2810 when bonded to the heater circuits 2830 shown in FIG. 29(a). The heater circuits 2830 are fabricated as an array of three LC tanks 2834 with the planar spiral coils 2832, each of which has an identical overall size (e.g., 3.8×4.4 mm$^2$) and an identical calculated inductance (e.g., about 95 nH). The resonance frequency $f_R$ values of the circuits 2830 are separated from each other by about 30 MHz by varying the size of the capacitors of the LC tanks 2834 (i.e., change the capacitance). Calculated values of the capacitance are 3.2 pF, 4.1 pF, and 5.3 pF; calculated values of resonant frequency $f_R$ are 225 MHz, 257 MHz, and 289 MHz. This relatively large frequency separation was selected to minimize the cross talk between the tanks; other frequency separations are also possible depending on the coil size and shape, the inductance, and the capacitance.

Fabrication of an SMA Microsyringe

Figure 30:
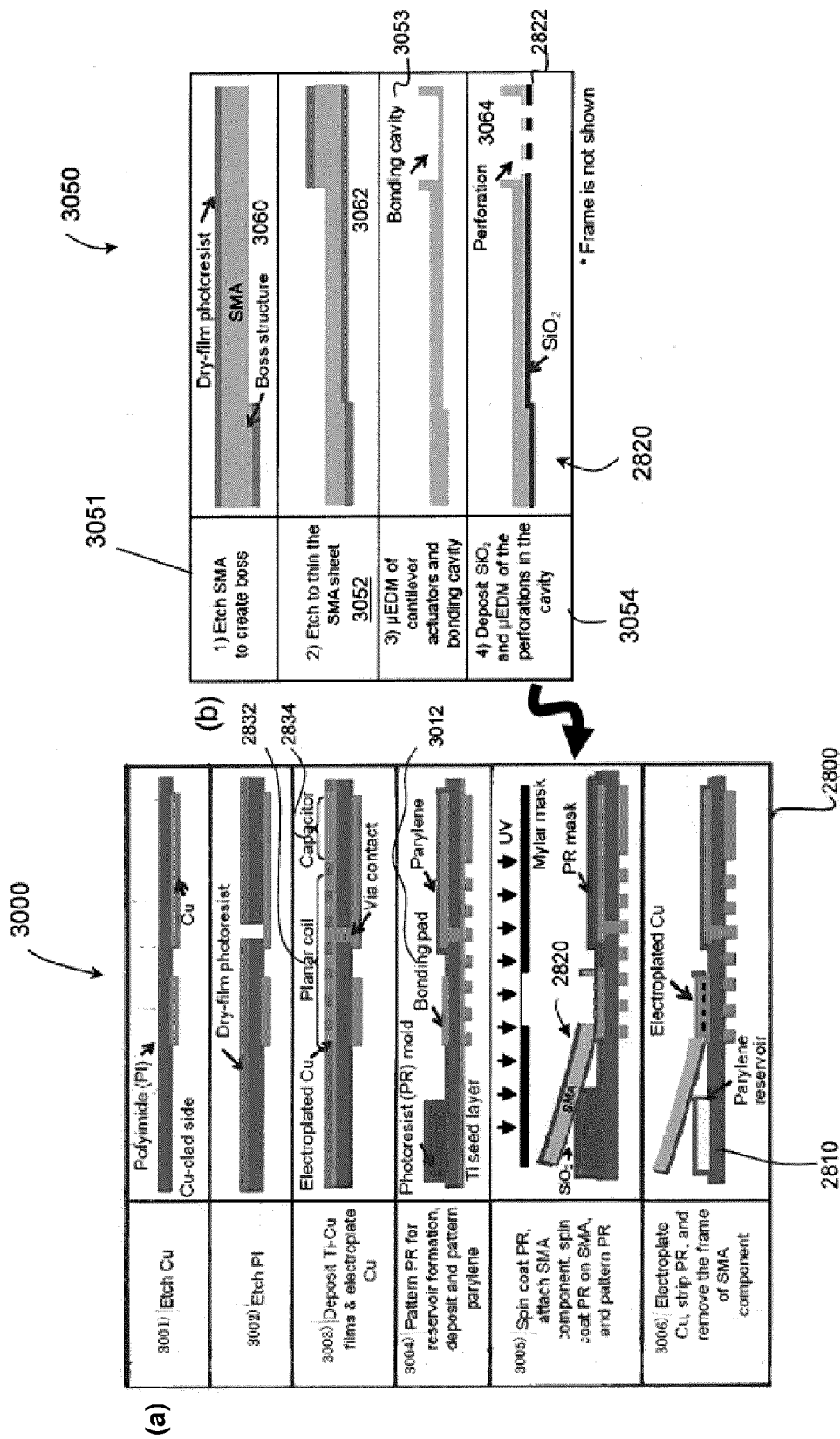
FIG. 30 shows a cross-sectional view of the fabrication process for (a) an illustrative wireless resonant circuit (steps 3001-3003), an illustrative reservoir formation (step 3004), and an illustrative SMA actuator assembly (steps 3005 and 3006), and (b) the illustrative SMA actuator component.

FIG. 30(a) shows a fabrication process 3000 for making the device 2800 of FIGS. 28 and 29. The planar LC heater circuits 2830 are fabricated using single-sided copper-clad polyimide (PI) film with 50 µm thickness: the copper is etched (step 3001), coated with dry-film photoresist (step 3002), and coated with titanium and copper films and electroplated with copper (step 3003) as described above with respect to FIGS. 3 and 15. After electroplating copper to form the heater coils 2832, the copper seed layer is etched away, leaving the titanium layer that will be used to provide the electrical connection for the later electroplating bonding of SMA. (The copper layer should be etched before the SMA bonding as the copper etchant, ferric chloride solution, attacks the SMA.) A 130 µm thick sacrificial mold for the reservoir formation is created on the backside of the substrate with three layers of spin-coated photoresist (SPR 220-7, Rohm and Haas Co., PA, USA) (FIG. 30(a), step 3004). The photoresist mold is then hard baked for two hours at 120° C.

Figure 31:
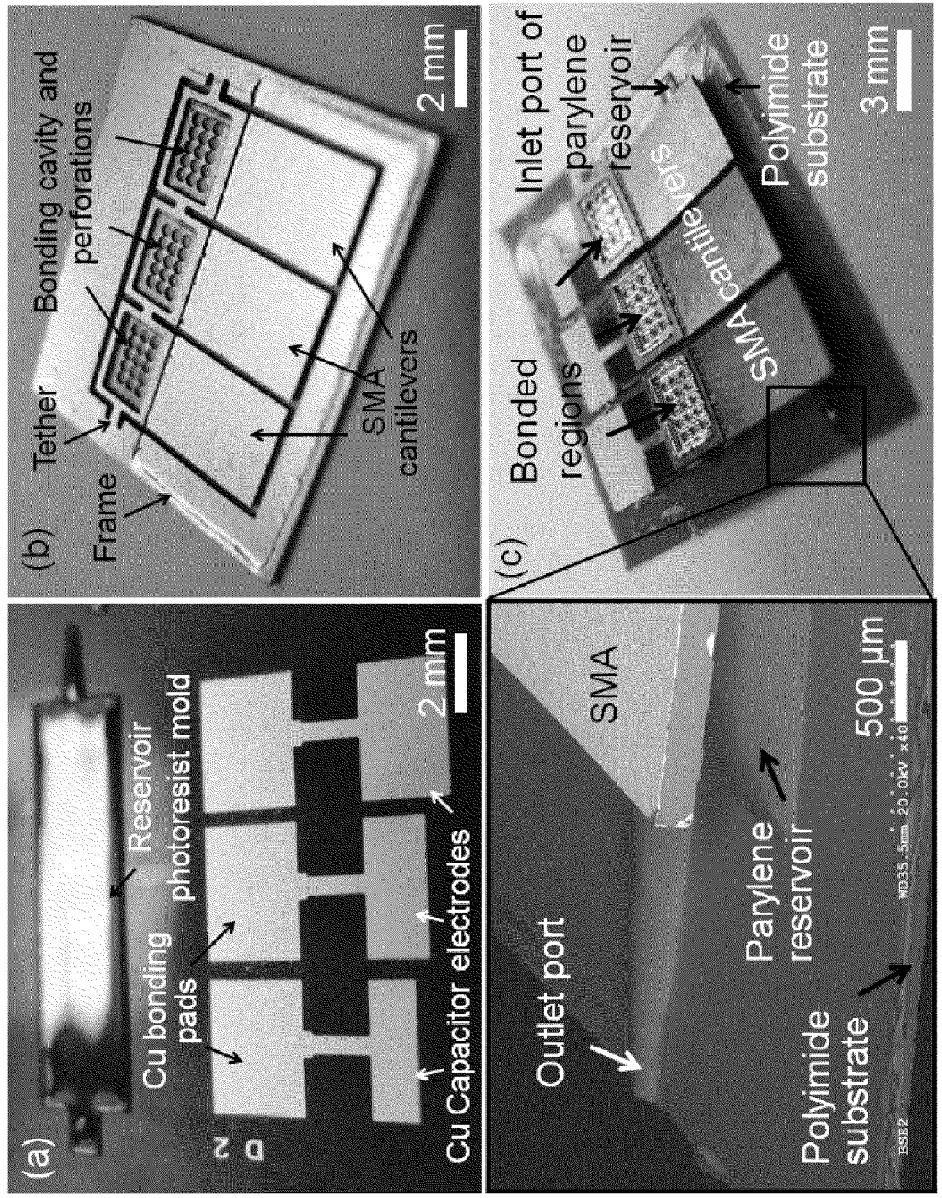
FIG. 31 shows results of the fabrication process shown in FIG. 30, including: (a) a sacrificial photoresist mold patterned for the reservoir and copper bonding pads for an SMA actuator assembly; (b) an illustrative SMA component fabricated by wet etching and μEDM; (c) a fabricated device with close-up of the parylene reservoir.

FIG. 31(a) shows the patterned photoresist mold with the copper-clad capacitor electrodes and bonding pads formed on the PI substrate. The reservoir walls are formed by depositing 10 μm thick Parylene-C (Specialty Coating Systems, IN, USA). To improve the parylene adhesion, the surfaces of the PI substrate is roughened using $O_2$ plasma at 100 W for 3 minutes prior to the parylene deposition. (The adhesion promoter $H_2O$:IPA:A-174(γ-methacryloxypropyl trimethoxy silane) commonly used for parylene attacks the sacrificial photoresist.) The parylene layer on the electroplating bonding pads for the SMA assembly is dry etched using a photoresist mask (FIG. 30(a), step 3004).

FIG. 30(b) illustrates a process 3050 of fabricating of the array of SMA actuators 2820 that is bonded to the heater circuits 2830 to form the device 2800. In step 3051, a 300 μm thick plate of the SMA is etched in hydrofluoric-nitric acid (HNA) for fifteen minutes to form a 15 μm high boss structure 3060 (to be located at the tips of the cantilever actuators 2820) using a laminated dry-film photoresist mask. This boss structure 3060 compensates for the thickness of the bonding pad on the substrate so that the SMA cantilevers 2820 achieve complete squeezing of the reservoir 2810 when actuated. Next, the SMA plate is etched from the other side in HNA to thin the structure down to about 100 μm while protecting the opposite side of the SMA (step 3052). The SMA plate is then patterned using micro-electro-discharge machining (μEDM, EM203, SmalTec International, IL, USA) to shape the cantilever structures 2820 and form a cavity 3062 and perforations 3064 (step 3053). FIG. 31(b) shows an illustrative patterned SMA plate; the actuator array is still tethered to the frame structure at this stage, for not only easier handling, but also high-precision assembly and bonding of each of the actuators to the heater circuit. A 3.5 μm thick $SiO_2$ film 2822, the compressive reset layer, is deposited on the bottom surfaces of the SMA actuators 2820 using a plasma-enhanced chemical vapor deposition process at an approximate temperature of 390° C. (step 3054).

The SMA actuator fabrication process 3050 yields actuators 2820 that can be bonded to the heater circuits 2830 in step 3005 of the device fabrication process 3000 in FIG. 30(a). The cavity regions 3062 of the SMA actuators 2820 are fixed onto bonding pads 3012 on the circuits 2830 coated with SPR-220 photoresist, which serves as a temporary adhesive for the SMA attachment. The photoresist is then soft baked for 10 minutes at 90° C., followed by spin coating of another layer of the photoresist on top of the SMA and its soft baking. After the photoresist on the cavity regions 3062 is removed with a lithography step, copper is electroplated in the cavity regions 3062 to grow 120 μm thick bonding structures through the perforations 3064, fixing the array of SMA actuators 2820 onto the heater circuits 2830 in step 3006. The photoresist layers, including the sacrificial mold inside the parylene reservoir 2810, are then dissolved using acetone in an ultrasonic bath. Lastly, the titanium seed layer is etched to complete the heater circuit fabrication, and the frame of the SMA actuators is removed by locally etching the tethers using μEDM as shown in FIG. 31(c). Heater circuits 2830a, 2830b, and 2830c of the fabricated device 2800 were measured to have a common inductance of 89 nH and capacitances of 3.3 pF, 4.2 pF, and 5.4 pF, respectively, and resonant frequencies of 231 MHz, 264 MHz, and 295 MHz, respectively, all of which match well with the calculated capacitance and resonant frequency values.

Exemplification of an SMA Microsyringe

Characterization results for the fabricated actuators including the multiple wireless-heater operation using frequency-modulated RF magnetic fields as well as thermal behaviors of the actuators are discussed below. The stepwise pH-level modification through the wireless control of the fabricated microsyringe device is experimentally demonstrated.

Selectable Activation of Wireless Heater Array

Figure 32:
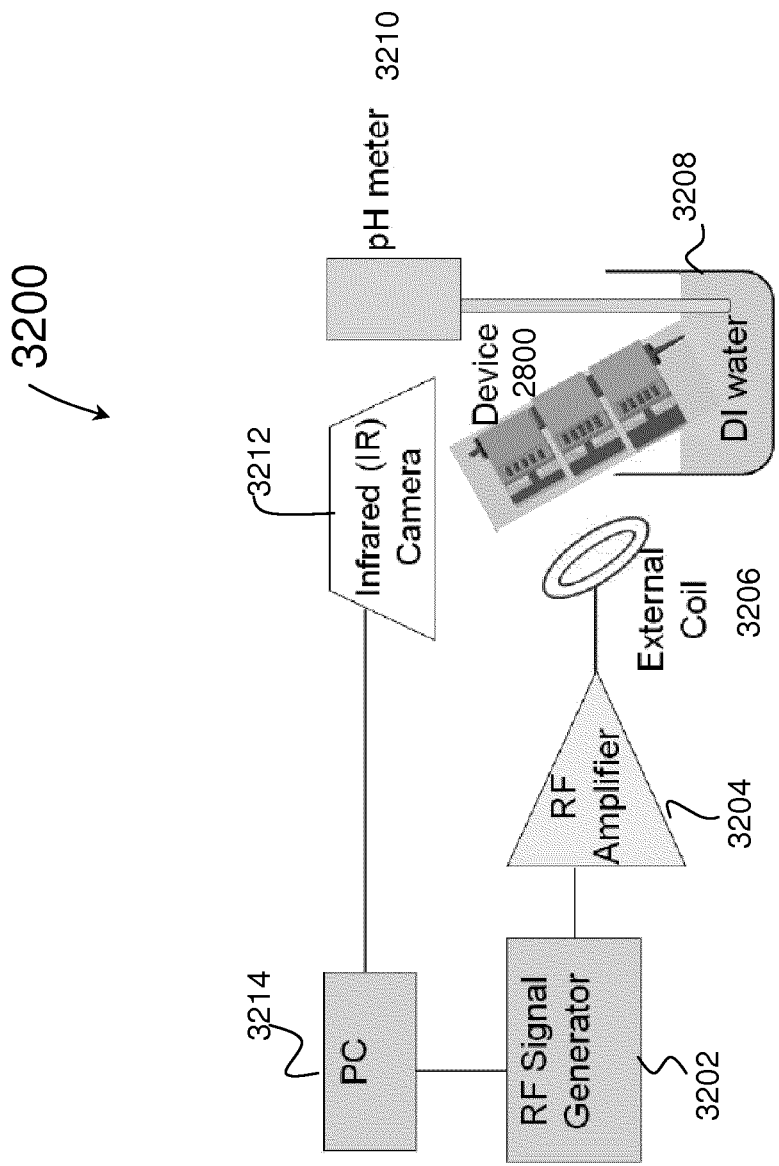
FIG. 32 shows an illustrative experimental setup for wireless testing of the illustrative fabricated devices of FIG. 31.

FIG. 32 illustrates a set-up 3200 for testing the device 2800 shown in FIGS. 28 and 29. A Labview™ program running on a PC 3214 controls the modulation frequency of an rf signal emitted by an rf signal generator 3202 (Hewlett-Packard 8657A). An rf amplifier 3204 coupled to the output of the rf signal generator 3202 amplifies the rf signal. The amplified RF signal drives an external coil 3206 to generate an rf magnetic field 10 that is applied to the device 2800 under test. An infrared camera 3212 (Jenoptik VarioCam HiRes 1.2M, Jena, Germany) captures images of the device 2800 and transmits the images to the PC 3214, which records and processes the images. In some tests, the device 2800 under test is at least partially submerged in a beaker 3208 of DI water, and a pH meter 3210 monitors the pH of the DI water in the beaker 3208.

Figure 33:
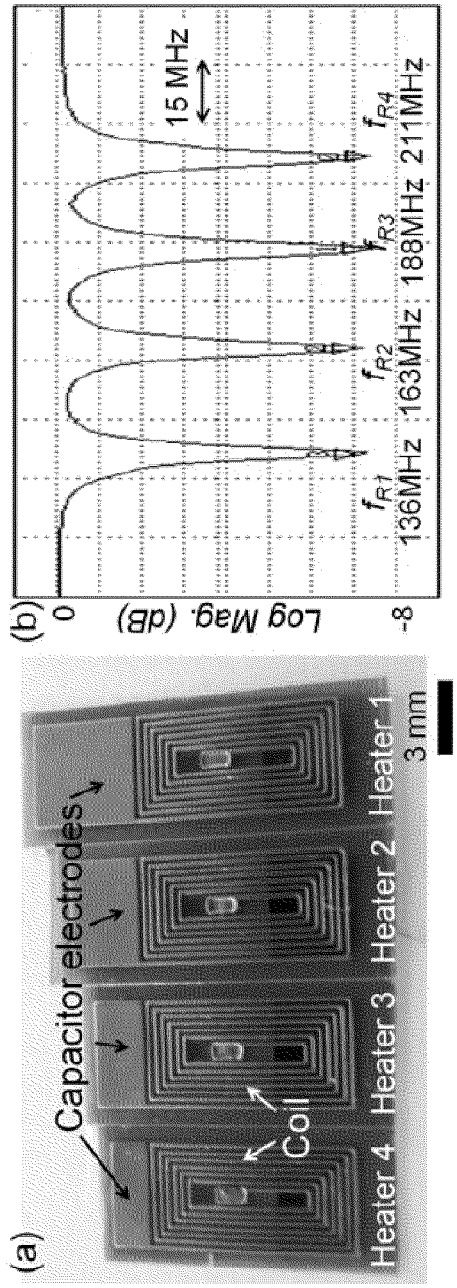
FIG. 33 shows (a) an illustrative array of four wireless heaters and (b) measured resonant frequencies of the four heaters.

In one test, the device 2800 included four heater circuits 2830, shown in FIG. 33(a), each of which had a different resonant frequency. The resonant frequencies of the heater circuits 2830 ($f_{R1-4}$) were wirelessly measured by connecting the external coil 3206 to a network analyzer (Agilent 4396B; not shown), adjusting the size of the external coil (23 mm diameter, about 900 nH) to cover the entire array of the heaters, driving the external coil 3206 with a chirped rf signal, and measuring the power reflected by the device 2800. This type of measurement is known in the art as an $S_{11}$ reflection parameter measurement. FIG. 33(b) is a plot of the device's $S_{11}$ reflection parameter, i.e., the logarithm of reflected power (normalized to transmitted power) versus signal frequency. The four dips in the reflected power are at the resonant frequencies of the heaters 2830. The measurement shows that $f_{R1}$, $f_{R2}$, $f_{R3}$, and $f_{R4}$, are 136, 163, 188, and 211 MHz, respectively.

Figure 34:
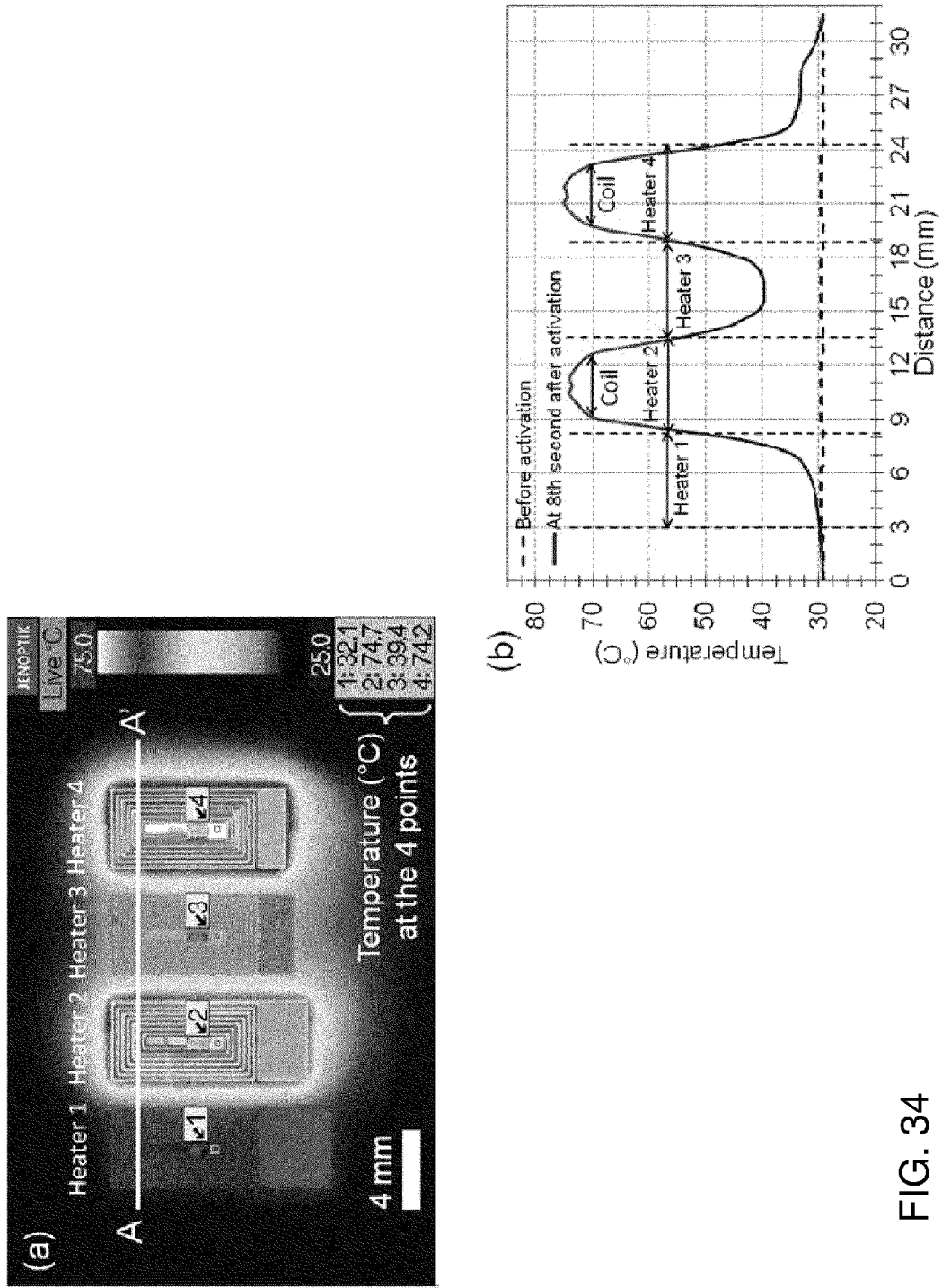
FIG. 34 shows (a) an infrared (IR) image showing selective wireless activation of illustrative Heaters-2 and -4 (the image was captured eight seconds after activation) and (b) the temperature distribution across the array of the four heaters along the line A-A' indicated in FIG. 34(a).

Next, two of the heater circuits were activated by modulating the magnetic field $f_M$ to switch between resonant frequencies $f_{R2}$ and $f_{R4}$ (i.e., the resonant frequencies of the second and fourth heaters) every 15 ms at an rf output power of 1 W. FIG. 34(a) shows an IR image of the heater circuit array captured with the IR camera 3212 at the eight seconds after the heater circuits were activated. FIG. 34(b) is a plot of the temperature along the line (A-A') indicated in FIG. 34(a) before heater activation (dashed line) and eight seconds after heater activation (solid line). The temperatures of the coil regions in Heaters 2 and 4 increased significantly, with a maximum temperature of about 75° C. on their coils, whereas the temperatures of the other heaters (Heaters 1 and 3) remained low. The average temperatures over the coil regions in Heaters 1, 2, 3, and 4 were measured to be 34.2° C., 66.3° C., 46.7° C., and 66.6° C., respectively. FIGS. 34(a) and (b) indicate that only the regions of the activated heaters reached the temperatures greater than the austenitic threshold temperature of the SMA (65° C.). The temperatures in the regions of the inactive heaters were low enough to keep the corresponding SMA inactive. Thus, selective activation of heater circuits through frequency modulation ensures that only the desired actuators are activated.

Heat Distribution in an SMA Cantilever Actuator

As described above, the SMA cantilever structure can be actuated by applying heat to one end of the structure. This leads to a thermal gradient across the structure due to heat loss, as well as a time delay in the heat transfer to the other end of the structure. These spatial and temporal characteristics in the heat transfer within the SMA structures are the important factors that affect their actuation behaviors. To characterize them, the temperature distribution and its change with time in an activated SMA cantilever were measured using the IR camera 1312. The cantilever actuator bonded to Heater 2 in the device shown in FIG. 31(*c*) was activated by tuning $f_M$ to the $f_{R2}$ value (264 MHz). The RF power used for this test was 0.15 W (approximately the minimum level required for the full-range actuation of the cantilever).

Figure 35:
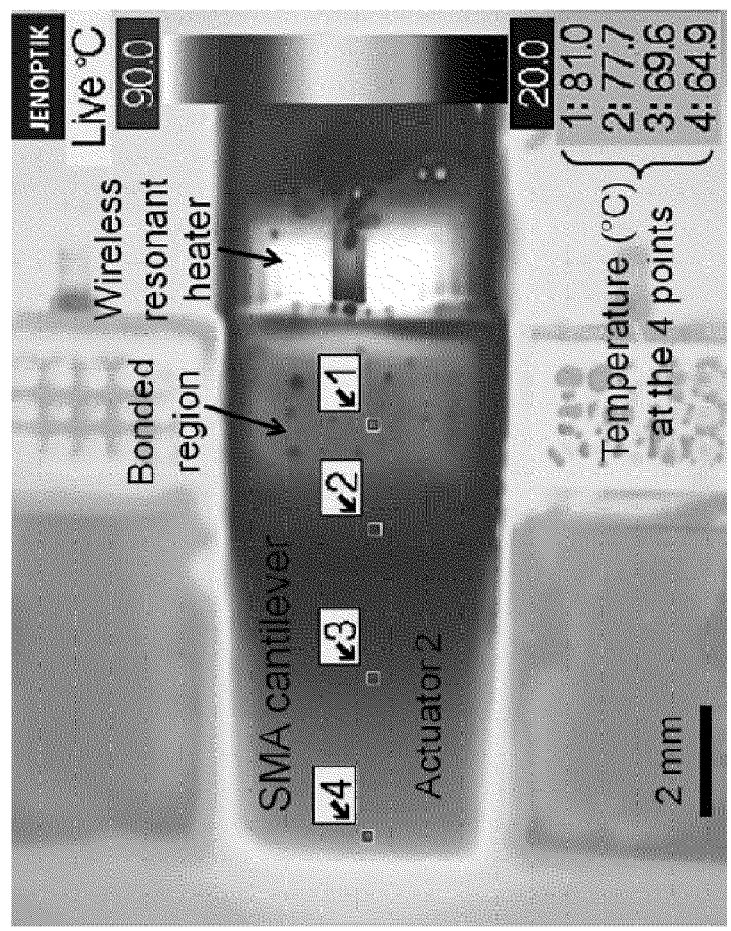
FIG. 35 shows an IR image of an illustrative SMA cantilever actuator with a wireless heater captured thirteen seconds after the heater activation.

FIG. 35 shows an IR image of the cantilever thirteen seconds after activation, which was when the temperature at the free end of the cantilever reached the SMA's threshold temperature of 65° C. and the actuator was fully activated. The IR image was processed to give temperatures of 81.0° C., 77.7° C., 69.6° C., and 64.9° C. at the points labeled 1, 2, 3 and 4, respectively, along Actuator 2 in FIG. 35. Point 1 is at the SMA bonding cavity covered by electroplated copper, point 2 is at the fixed end of the cantilever, point 3 is at a middle location (2.5 mm away from the point 2) of the cantilever, and point 4 is at the free end (5 mm away from the point 2) of the cantilever.

Figure 36:
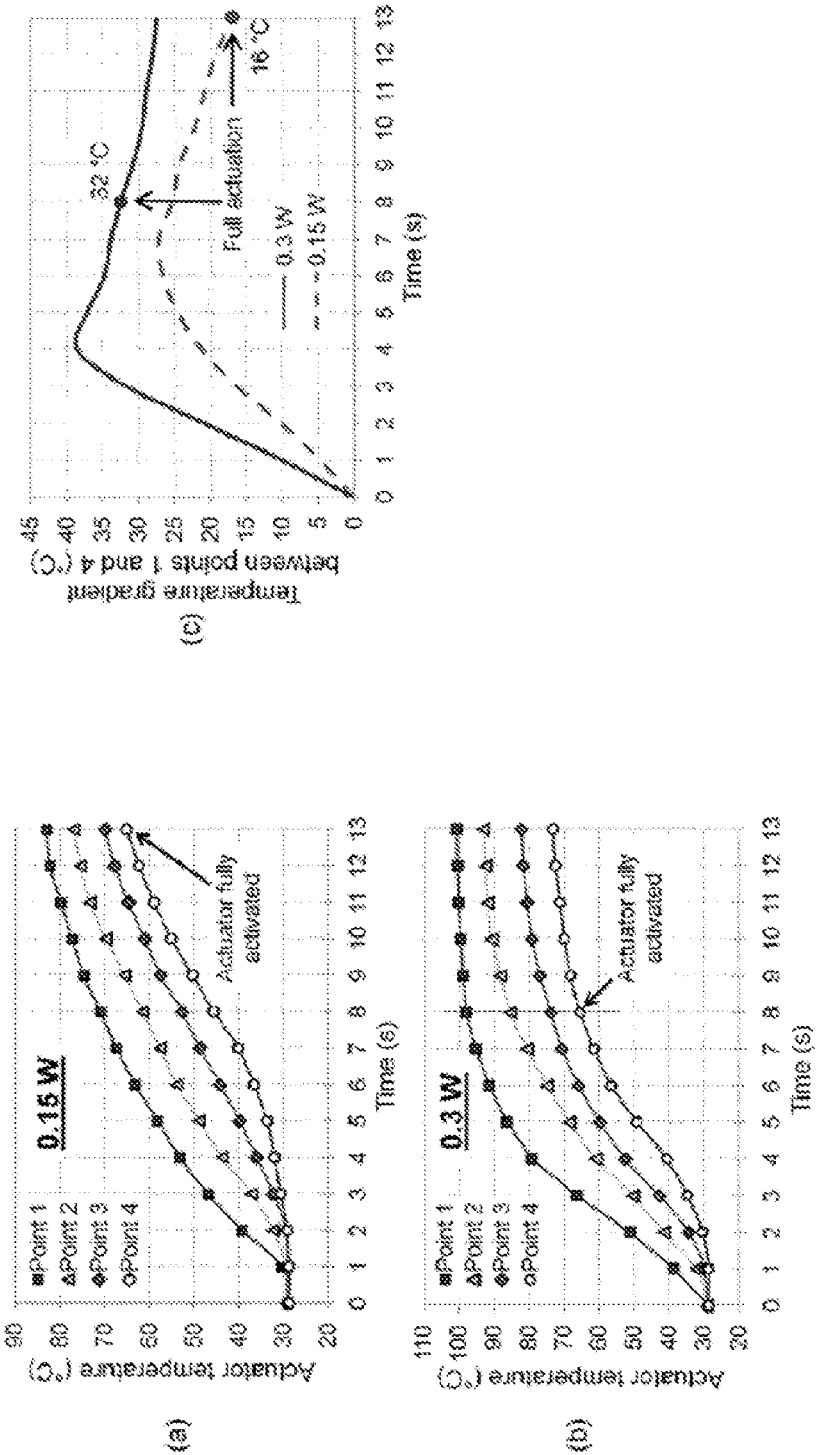
FIG. 36 shows measured temporal changes in the temperature of the illustrative SMA cantilever actuator of FIG. 35 at the points 1-4 (labeled in FIG. 35) when the heater is resonated wirelessly with RF output power of (a) 0.15 W and (b) 0.3 W, along with (c) temporal changes in temperature gradients between the bonding cavity (point 1) and the free end of the cantilever (point 4) for the 0.3 W and 0.15 W cases obtained from the results in FIGS. 36(a) and 36(b).

Transient temperatures measured at these four points for the time period of 13 seconds are plotted in FIG. 36(*a*). FIG. 36(*b*) shows the same measurement at twice the RF power (i.e., 0.3 W). FIG. 36(*c*) is a plot of the temperature gradient from point 1 to point 4 across the SMA cantilever beam as a function of time from activation at both 0.15 W (dashed line) and 0.3 W (solid line). The temperature gradient is higher at higher RF power and peaks at about four seconds after activation for 0.3 W.

Table 2 (below) shows the average rate of temperature increase, full-actuation time, and temperature gradient between points 1 and 4 for RF power levels of 0.15 W and 0.3 W. The temperature gradient at the full-actuation time with 0.3 W was measured to be twice the gradient for the case with 0.15 W. This indicates that, although increasing the RF output power improves the temporal response of the actuator, it also leads to a higher temperature at the fixed end of the cantilever in order to achieve full actuation. Low operational temperatures are required in many cases, especially those in biomedical areas. To minimize heat produced and its dissipation to the external environment, the RF power level should be optimized in conjunction with selection of SMA materials that have lower threshold temperatures as well as with proper device packaging.

TABLE 2

Measured actuator response at 0.15 and 0.3 W power levels.

| RF Power | Average rate of temperature increase (° C./s) | Time for full actuation (s) | Temperature gradient between points 1 and 4 (° C.) |
|---|---|---|---|
| 0.15 W | 4.1 | 13 | 16 |
| 0.3 W | 8.6 | 8 | 32 |

Wireless Tests for SMA Microsyringes

Figure 37:
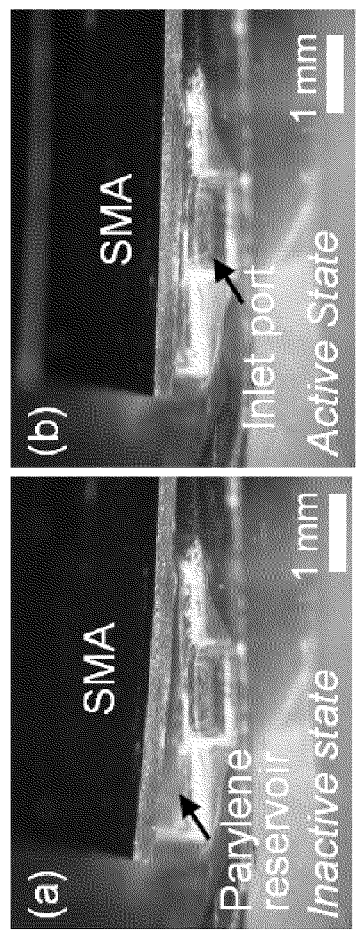
FIG. 37 shows side views of the illustrative SMA cantilever actuator of FIG. 35 in (a) an inactive state in which the SMA cantilever actuator is separated from a reservoir and (b) an active state in which the SMA cantilever actuator squeezes the reservoir.

Preliminary wireless tests for the fabricated microsyringe devices were experimentally performed using the set-up 3200 illustrated in FIG. 32. The external coil 3206 was placed at a distance of about 8 mm from the device 2800 in this experiment. The wireless activation of individual actuators 2820 through modulation frequency $f_M$ tuning was tested first. FIGS. 37(*a*) and 37(*b*) show side views of the third actuator (Actuator 3 in FIG. 29(*a*)) in its relaxed (inactive) state without an external field and in its actuated (fully active) state with an external field at $f_M=f_{R3}$, respectively. When actuated, the SMA actuator squeezes the parylene reservoir, as shown in FIG. 37(*b*). The maximum force at the free end of the actuator was measured to be about 840 mN using a digital force gauge (DS2-1, Imada Inc., IL, USA) with a 1-mN resolution.

Device tests were further conducted to demonstrate the wireless control of the pH level of liquid. This was implemented by ejecting controlled amounts of a pH buffer from the device's reservoir 2810 to DI water using three actuators 2820. A device 2800 with three heater circuits 2830 having measured resonance frequencies $f_{R1}$, $f_{R2}$, and $f_{R3}$ of 231 MHz, 264 MHz, and 295 MHz, respectively, was used for this experiment. The reservoir 2810 was fully filled with about 5 µL of pH-2 buffer solution (SB96-500, Fisher Scientific, ON, Canada) through an inlet port using a syringe needle, and then the inlet port was sealed with silicone adhesive. The device 2800 was placed in a beaker 3208 with 10 ml of DI water so that the outlet port of the reservoir 2810 was immersed in the DI water, and the pH value of the DI water was measured during the test using a pH meter as shown in FIG. 32. The stepwise ejections of the buffer solution from the reservoir 2810 were implemented through the following three steps with a 1-minute interval (each step took about 1 minute): (1) Actuator 3 was activated by tuning $f_M$ to the $f_{R3}$ value, squeezing one-third of the area of the reservoir 2810; (2) Actuators 3 and 2 were simultaneously activated by modulating $f_M$ to the $f_{R3}$ and $f_{R2}$ values alternately for an equal time period of 15 ms, squeezing another third of the area of the reservoir 2810; (3) Actuators 3, 2, and 1 were all activated by modulating $f_M$ to the three $f_R$ values in the same manner, squeezing the last third of the area of the reservoir 2810.

In step (1), an RF output power of 0.25 W was sufficient for full squeezing with Actuator 3. When two or more actuators are involved, as in steps (2) and (3), the duty cycle of actuator excitation drops from 100% to 50% or less, causing heat loss during each "off" time in the cycle. The actuator temperature decreases more as the number of actuators increases, i.e., the off time in each actuator becomes longer. In order to compensate for this condition, the RF power in steps (2) and (3) was adjusted to higher levels (1.2 and 3.2 W, respectively) to ensure full squeezing.

A substantially larger power (4.8×) was used in step (2) than in step (1) to compensate for the lower duty cycle (50% versus 100%) in step (2) than in step (1). The power used in step (3) was 2.67× larger than that in step (2), although the single-actuator duty cycle (33%) in step (3) was only two-thirds the single-actuator duty cycle in step (2). The different powers may be selected to compensate for a variety of device behaviors, including non-uniform power transfer to the heaters/actuators due to their different locations with respect to the external coil, as well as a slight delay in frequency settling observed when the RF signal generator used switches the frequency (affecting the duty cycle).

Figure 38:
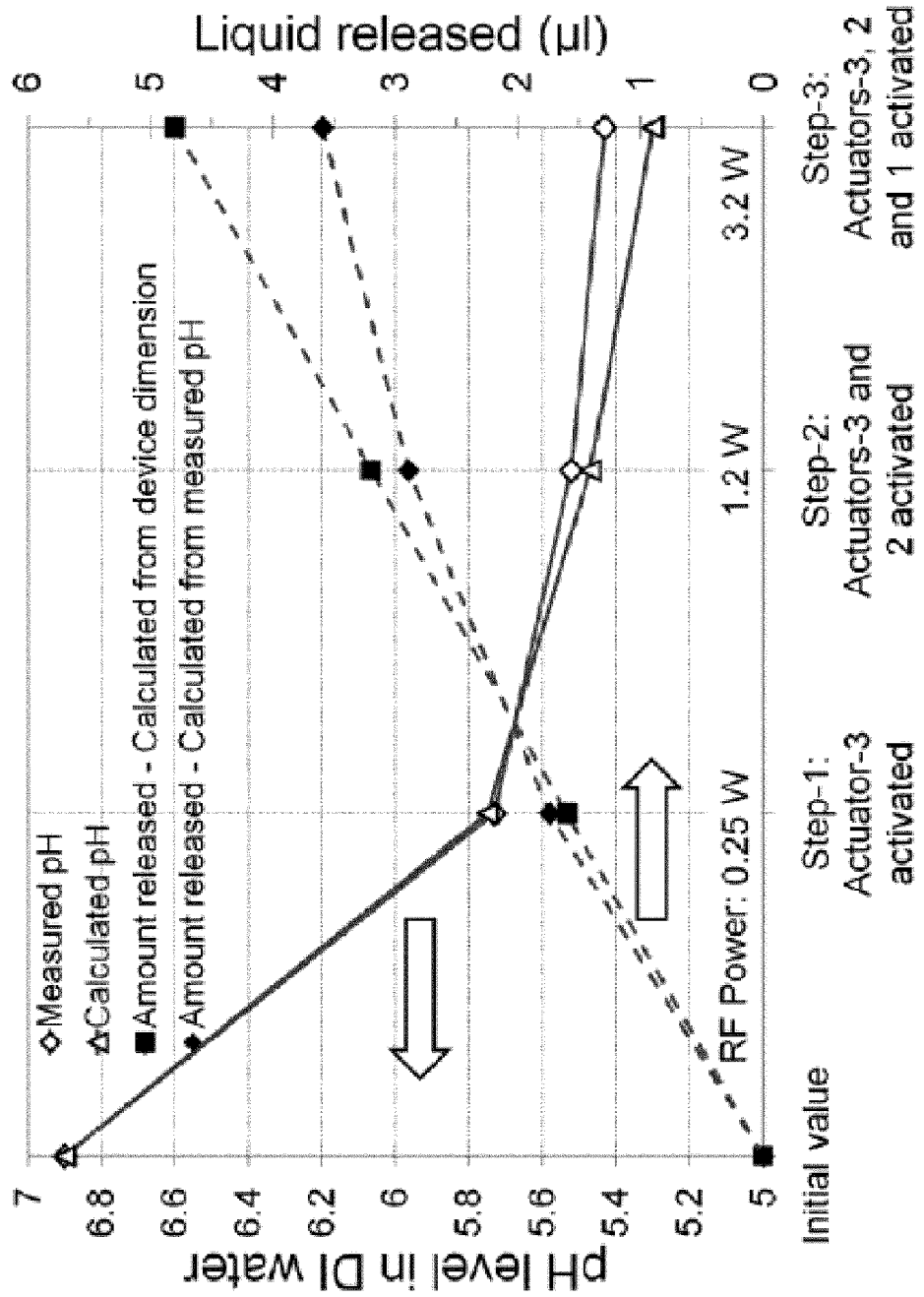
FIG. 38 is a plot of change in pH (left axis) and released amounts of pH buffer (right axis) versus the number of activated actuators for the illustrative device of FIG. 37.

FIG. 38 is a plot of the measured pH value (left axis) and the calculated amount of released solution (right axis) versus time (actuation step). The pH measurement indicates a consistent reduction from the initial pH value of 6.90 to the final value of 5.43 due to the release of the acidic buffer solution. FIG. 38 also shows the calculated volume of the released solution (calculated with the reservoir and actuator sizes, i.e., release volume of 4.1×3×0.13 mm³ per step) and a pH value calculated from the theoretical released volume after each actuation step. The dissolution of atmospheric $CO_2$ in DI water is known to affect its pH value—it was verified that this effect was negligible for the time period involved in the experiment. Both the measured pH values and the released amounts calculated using the pH values agree with the corresponding theoretical values defined above. Small deviations seen in steps (2) and (3) may be related to the incompleteness in the reservoir squeezing, which can be caused by various non-ideal factors such as variations in the height of the bonded actuators and slight bending of the PI substrate.

Flow diagrams are used herein. The use of flow diagrams is not meant to be limiting with respect to the order of operations performed. The subject matter described herein sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to, e.g., physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A microfluidic device comprising:
   a reservoir to hold a substance, wherein the reservoir includes a release hole to dispense the substance;
   a hydrogel microvalve disposed within the release hole, wherein the hydrogel microvalve comprises a photosensitive hydrogel that is cured via ultraviolet radiation; and
   a resonant heater in thermal communication with the hydrogel microvalve to actuate the hydrogel microvalve, wherein the resonant heater is configured to absorb alternating current electromagnetic energy at only a predefined resonance, wherein the predefined resonance has a center frequency between of 10 MHz and 1 GHz, to power the resonant heater.

2. The microfluidic device of claim 1, wherein the substance is a fluid.

3. The microfluidic device of claim 1, wherein the substance is a powder.

4. The microfluidic device of claim 1, wherein the substance is a drug.

5. The microfluidic device of claim 1, wherein the hydrogel microvalve is self-aligned to the release hole.

6. The microfluidic device of claim 1, wherein the hydrogel microvalve comprises at least one of poly(N-isopropylacrylamide), poly(N,N-dimethylacrylamide-co-N-phenylacrylamide), and poly(glycidyl methacrylate-co-N-isopropylacrylamide).

7. The microfluidic device of claim 1, wherein the resonant heater is a planar resonant heater.

8. The microfluidic device of claim 1, wherein the predefined resonance has an active width between 1 kHz and 10 MHz.

9. The microfluidic device of claim 1, wherein the release hole is a first release hole, the hydrogel microvalve is a first hydrogel microvalve, the resonant heater is a first resonant heater configured to absorb electromagnetic energy at a first resonant frequency so as to actuate the first hydrogel microvalve, and further comprising:
   a second release hole formed in the reservoir;

a second hydrogel microvalve disposed with the second release hole to prevent the substance from transiting the second release hole; and a second resonant heater configured to absorb electromagnetic energy at a second resonance frequency so as to actuate the second hydrogel microvalve.

10. A method of fabricating a hydrogel microvalve, the method comprising:

filling a reservoir having first and second release holes with a photosensitive hydrogel;

exposing the first release hole to ultraviolet radiation to cure photosensitive hydrogel disposed within the first release hole; and withdrawing uncured photosensitive hydrogel from the reservoir via the second release hole to form the cured photosensitive hydrogel in the first release hole into a hydrogel microvalve.

11. The method of claim 10, wherein the photosensitive hydrogel comprises at least one of poly(N-isopropylacrylamide), poly(N,N-dimethylacrylamide-co-N-phenylacrylamide), and poly(glycidyl methacrylate-co-N-isopropylacrylamide).

12. The method of claim 10, wherein exposing the first release hole to ultraviolet radiation includes adjusting at least one of an exposure time and an exposure intensity to control dimensions of the hydrogel microvalve.

13. The method of claim 10, wherein an interior surface of the reservoir is formed or coated with polyimide, and further comprising:

treating the interior surface with an oxygen plasma before filling the reservoir with the photosensitive hydrogel to prevent adhesion of the photosensitive hydrogel to the interior surface.

14. The method of claim 10, further comprising:

placing a resonant heater in thermal communication with the hydrogel microvalve.

15. The method of claim 14, further comprising absorbing, by the resonant heater, alternating current electromagnetic energy only at a predefined resonance.

* * * * *